US012749562B2

(12) United States Patent
Salazar

(10) Patent No.: US 12,749,562 B2
(45) Date of Patent: Sep. 29, 2026

(54) SYSTEM AND METHOD OF MANAGING, REMINDING, AND DISPENSING MEDICATION FROM A CONTROLLED-ACCESS CONTAINER

(71) Applicant: Scott J. Salazar, North Richland Hills, TX (US)

(72) Inventor: Scott J. Salazar, North Richland Hills, TX (US)

( * ) Notice: Subject to any disclaimer, the term of this patent is extended or adjusted under 35 U.S.C. 154(b) by 0 days.

(21) Appl. No.: 18/109,221

(22) Filed: Feb. 13, 2023

(65) Prior Publication Data

US 2023/0260615 A1 Aug. 17, 2023

Related U.S. Application Data

(60) Provisional application No. 63/309,424, filed on Feb. 11, 2022.

(51) Int. Cl.
*G16H 20/13* (2018.01)
*G16H 15/00* (2018.01)
*G16H 40/20* (2018.01)

(52) U.S. Cl.
CPC ............. *G16H 20/13* (2018.01); *G16H 15/00* (2018.01); *G16H 40/20* (2018.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS 7,004,324 B1 2/2006 Delorio
7,344,047 B2 3/2008 Gilmore
(Continued)

OTHER PUBLICATIONS

Tsai et al. 2010, "iMAT: Intelligent medication administration tools," The 12th IEEE International Conference on e-Health Networking , Applications and Services, Lyon, France, 2010, pp. 308-315, doi: 10.1109/HEALTH.2010.5556551.*
(Continued)

*Primary Examiner* — Robert W Morgan
*Assistant Examiner* — Charles P Coleman
(74) *Attorney, Agent, or Firm* — Osha Bergman Watanabe & Burton LLP

(57) ABSTRACT

A system and a method of managing, reminding, and dispensing medication from a controlled-access container enable the controlled consumption of medication. The method utilizes a computerized medication container including a processor, a monitoring camera, and a mechanical switch. A container-interaction event is recorded with the monitoring camera, if the mechanical switch is actuated by the computerized medication container being in a physically-opened configuration. The container-interaction event is relayed from the monitoring camera, through the processor, and to the central computing system, if the container-interaction event is recorded. The container-interaction event is chronologically appended into a container event log with the central computing system. A container-interaction alert is then generated based on the container-interaction event with the central computing system. The container-interaction alert is relayed from the central computing system to a user personal computing (PC) device. Then, the container-interaction alert is outputted with the corresponding user PC device.

21 Claims, 24 Drawing Sheets

(58) Field of Classification Search
CPC ........ G16H 20/13; G16H 20/17; G16H 30/00; G16H 40/00; G16H 50/00; G16H 70/00; G16H 40/20; G06Q 50/22–24
USPC .................................................. 705/2, 3, 20
See application file for complete search history.

(56) References Cited

U.S. PATENT DOCUMENTS

| | | | | |
|---|---|---|---|---|
| 9,501,626 | B2 | 11/2016 | Zhang | |
| 2005/0209733 | A1* | 9/2005 | Gilmore | G16H 20/13 700/231 |
| 2006/0079994 | A1* | 4/2006 | Chu | G07F 11/62 700/231 |
| 2008/0059228 | A1* | 3/2008 | Bossi | G16H 30/20 705/2 |
| 2010/0185456 | A1 | 7/2010 | Kansal | |
| 2012/0130534 | A1* | 5/2012 | Wurm | G07F 17/0092 700/236 |
| 2013/0030566 | A1* | 1/2013 | Shavelsky | A61J 7/04 221/154 |
| 2013/0335193 | A1* | 12/2013 | Hanson | G07C 9/00174 340/5.61 |
| 2016/0132660 | A1* | 5/2016 | Barajas | G16H 30/40 705/2 |
| 2017/0087059 | A1 | 3/2017 | Rodriguez et al. | |
| 2018/0333335 | A1 | 11/2018 | Carson et al. | |
| 2020/0085694 | A1* | 3/2020 | Patel | G08B 21/24 |
| 2021/0182646 | A1* | 6/2021 | Kaczmarz | G06K 19/07726 |

OTHER PUBLICATIONS

Da Silva et al. 2019, "Devices-Based System Designed to Improve the Treatment Adherence of Hypertensive Patients," Sensors (Basel). Oct. 18, 2019;19(20):4539. doi: 10.3390/s19204539. PMID: 31635394; PMCID: PMC6832274.*

Digital Pill Box and Reminder for Mom, Retrieved from Internet, Retrieved on Feb. 13, 2023 <URL: https://www.igp.com/p-digital-pill-box-and-reminder-for-mom-149579>.

Never Miss Your Pills Again!, Retrieved from Internet, Retrieved on Feb. 13, 2023 <URL: https:/elliegrid.com/>.

* cited by examiner

SYSTEM AND METHOD OF MANAGING, REMINDING, AND DISPENSING MEDICATION FROM A CONTROLLED-ACCESS CONTAINER

The current application claims a priority to the U.S. provisional patent application Ser. No. 63/309,424 filed on Feb. 11, 2022. The current application is filed on Feb. 13, 2023, while Feb. 11, 2023, was on a weekend.

FIELD OF THE INVENTION

The present invention relates generally to monitoring methods and healthcare systems. More specifically, the present invention provides a system and a method that facilitates users to monitor and control the consumption of medication stored in a controlled-access container by measuring and supporting end-user medication consumption case metrics and conformance.

BACKGROUND OF THE INVENTION

Nowadays, most medication must be taken as prescribed to increase the efficiency of the medication as well as to prevent undesired side-effects. For example, if medication for a virus is not taken as prescribed, the virus can become resistant to the effects of the medication. Oftentimes, the patient forgets to take the medication or takes the wrong amount of medication if they were not reminded to do so. While this is often not a problem in a controlled environment, unless the patient is hospitalized, a caregiver cannot be always present to keep track of the medication consumption by the patient. There are some tools users can utilize to keep track of medication consumption by the user or other users, such as mobile applications. However, most of these tools cannot accurately keep track of the medication consumption of a patient in real time. Therefore, there is a need for a system and a method that helps users monitor and control the medication consumption of various users.

An objective of the present invention is to provide a system and a method of managing, reminding, and dispensing medication from a container. By utilizing the present invention, the user can ensure that other users or themselves take the right amount of medication on time as prescribed. The present invention has the capability of alarming and reminding the users when the medication needs to be taken. Further, the present invention allows the users to monitor the medication consumption. The system of the present invention is equipped to monitor the actions of the user when the user proceeds to take the medicine which can be recorded for record keeping. Additional features and benefits are further discussed in the sections below.

SUMMARY OF THE INVENTION

The present invention provides a system and a method of managing, reminding, and dispensing medication from a controlled-access container. The present invention allows users to securely store medications in such a way that the medication can be monitored, and the medication consumption can be controlled. The present invention allows the safe and correct consumption of medicine by any user. In a preferred embodiment, the system of the present invention includes a computerized medication container that can be customized to properly store the desired medication. The computerized medication container can be equipped with a mechanical switch and a monitoring camera that help monitor when the computerized medication container is opened and record that event, respectively.

The recording of the medication consumption can be used for record-keeping to track the medication consumption habits to ensure that the user is taking the right amount of medication at the prescribed schedule. In addition, the recording of the medication consumption can be transmitted to authorized users, such as nurses or caregivers, to enable the authorized users to monitor the users taking the medicine. Furthermore, the computerized medication container can be equipped with notification means to help the user know when or how to take the medication. For example, the computerized medication container can be equipped with auditory or visual notification means that output a reminder to take the medication. The system of the present invention can also include means to notify the authorized users of the users' actions so that the authorized users can monitor the medication consumption of the users.

BRIEF DESCRIPTIONS OF THE DRAWINGS

DETAIL DESCRIPTIONS OF THE INVENTION

All illustrations of the drawings are for the purpose of describing selected versions of the present invention and are not intended to limit the scope of the present invention.

Figure 1:
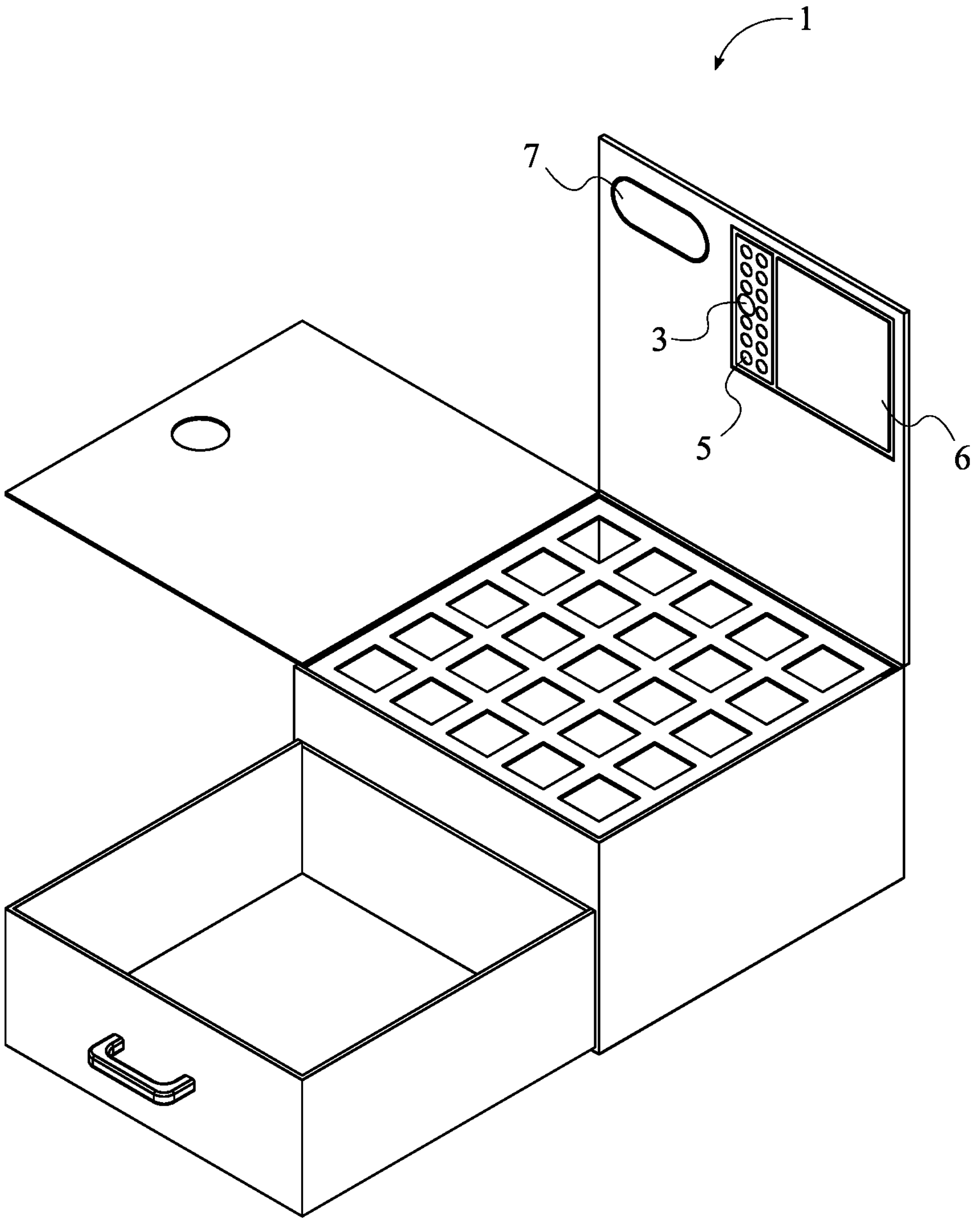
FIG. 1 is a top perspective view of a computerized medication container of the system of the present invention, wherein the computerized medication container is shown in a physically-opened configuration.
Figure 2:
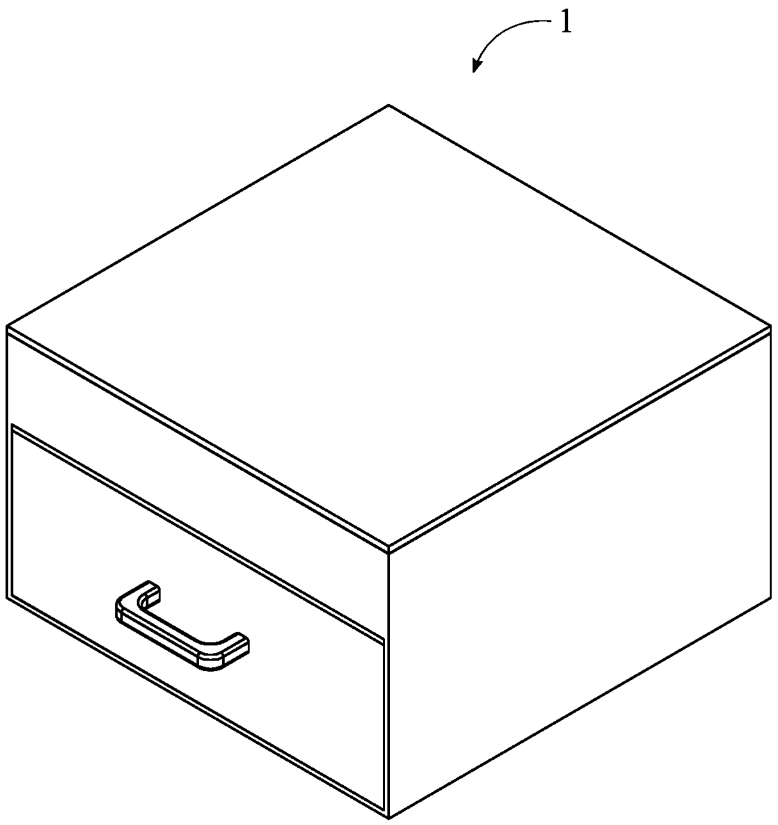
FIG. 2 is a top perspective view of the computerized medication container of the system of the present invention, wherein the computerized medication container is shown in a physically-closed configuration.
Figure 3:
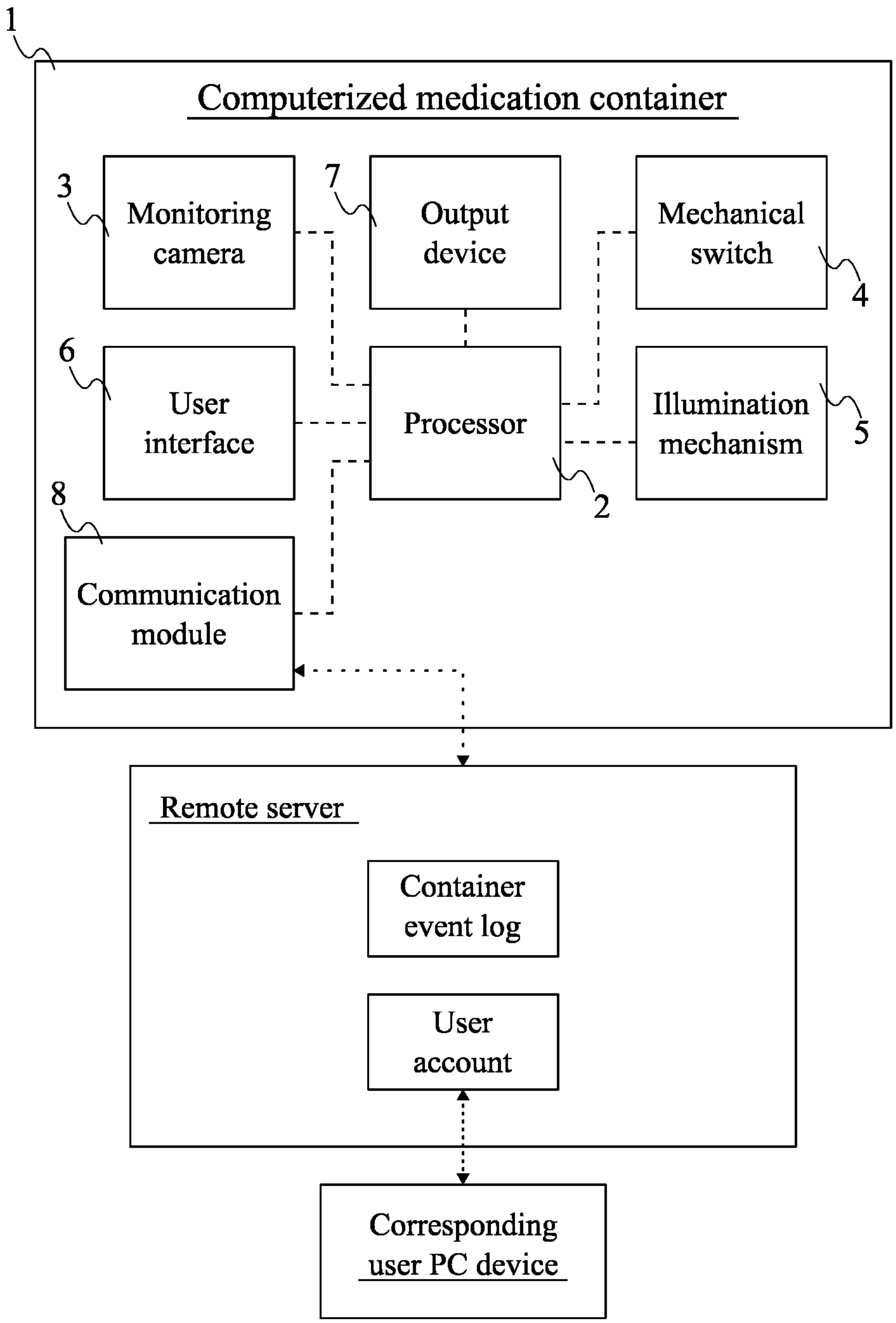
FIG. 3 is a schematic view showing the overall system of the present invention.

The present invention is a system and a method of managing, reminding, and dispensing medication from a controlled-access container. The present invention enables the safe and controlled medication consumption by users and enables authorized users, such as caregivers, to monitor the correct consumption of the medication by the users. The present invention also enables the generation of positive medication consumption case conformance. As can be seen in FIG. 1 through 3, the system used to implement the method of the present invention is provided with at least one computerized medication container 1 (Step A). The computerized medication container 1 is a customizable container structure that can be configured to store various medications. The computerized medication container 1 can also be customized to be used in different environments. For example, the computerized medication container 1 can be provided as a portable suitcase that can be carried along. The portable suitcase embodiment can include integrated power source to enable the operation of the computerized medication container 1. The computerized medication container 1 can also be provided as a fixed furniture piece, such as a top box or cabinet, to permanently store medication at a desired location. The computerized medication container 1 can also be provided as a portable furniture piece that can be plugged to any available power source at the user's location to store the desired medication.

As can be seen in FIG. 1 through 3, the computerized medication container 1 further includes at least one processor 2, at least one monitoring camera 3, at least one mechanical switch 4, and a user interface 6. The processor 2 performs the computations necessary for the monitoring and recording of the user's interactions with the computerized medication container 1 using the mechanical switch 4 and the monitoring camera 3, respectively. The monitoring camera 3 and the mechanical switch 4 are electronically connected to the processor 2 to transmit the recording data and the electrical signals, respectively. The monitoring camera 3 enables the recording of the user's interactions with the computerized medication container 1, such as taking any stored medication, to enable authorized users (i.e., such as a caregiver), and to monitor the user's interactions. The mechanical switch 4 enables the automatic activation of the computerized medication container 1 so that the necessary processes can be performed once the user interacts with the computerized medication container 1. This provides some privacy to the user when the user is not interacting with the computerized medication container 1 and helps save energy.

As can be seen in FIG. 1 through 3, the user interface 6 is designed to enable the direct configuration of the various settings of the computerized medication container 1. Any reminders or alerts generated by the present invention can be directly displayed on the user interface 6 or communicated to the authorized users via third-party services. For example, any reminder or alert could be transmitted to the authorized users via different communication services such as text messaging services, email services, etc. Further, any data compiled and processed by the present invention can be exported and/or published to any format compatible with third-party services that are available to the authorized users. The user interface 6 can be configured to enable the wireless communication between users. Furthermore, the computerized medication container 1 can include a communication module 8 which enables the processor to transmit data to a central computing system or other computing devices as well as to receive data. The central computing system can be a computing system integrated into the computerized medication container 1 so that any processes and computations are performed locally. Further, the computerized medication container 1 can be a remote server that is wirelessly coupled to the processor 2 using the communication module 8. The communication module 8 can utilize different wireless protocols including, but not limited to, 4G/5G ethernet and two-way Radio Frequency (RF) technologies.

Figure 4:
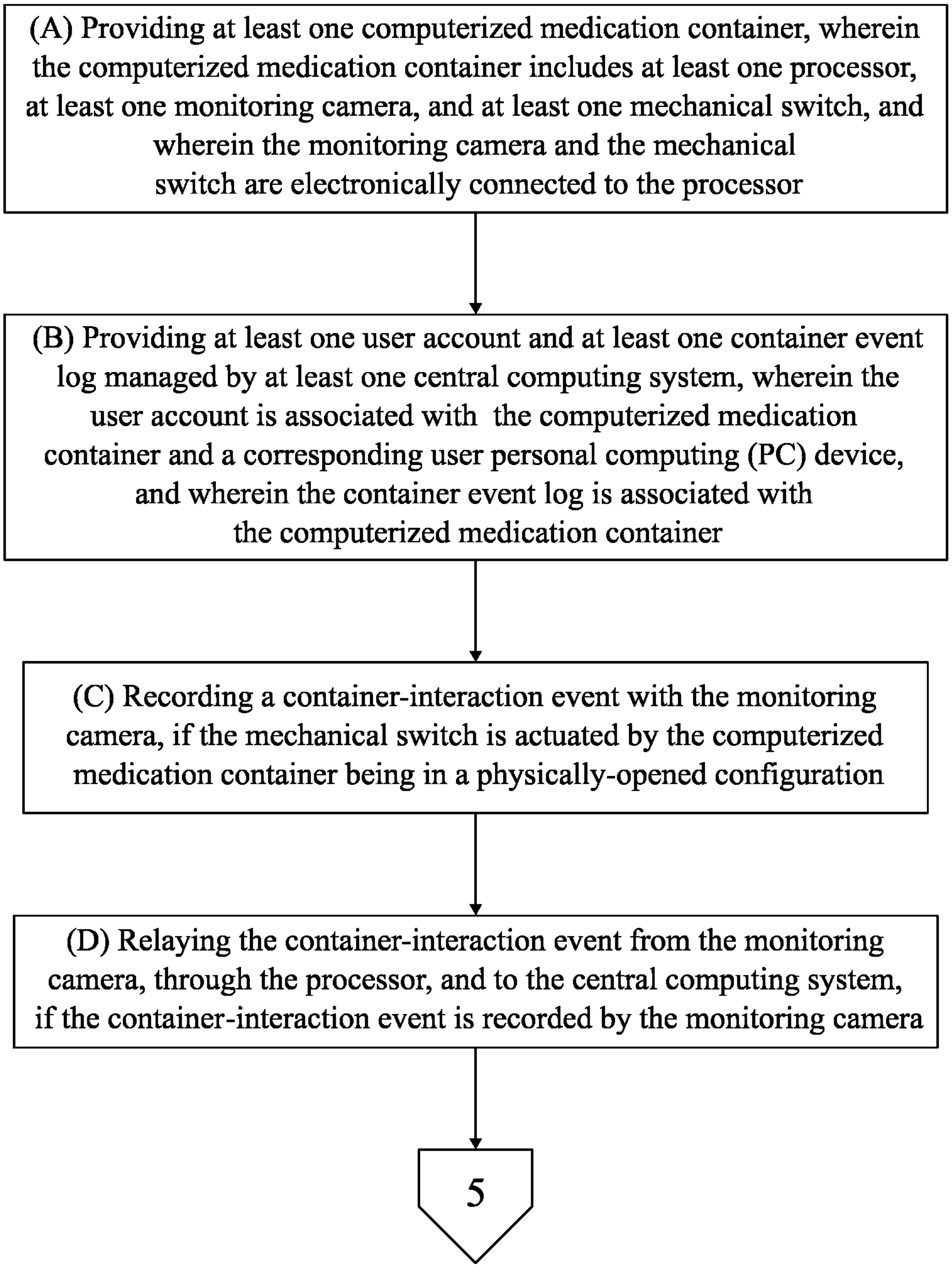
FIG. 4 is a flowchart depicting the overall process of the present invention.
Figure 5:
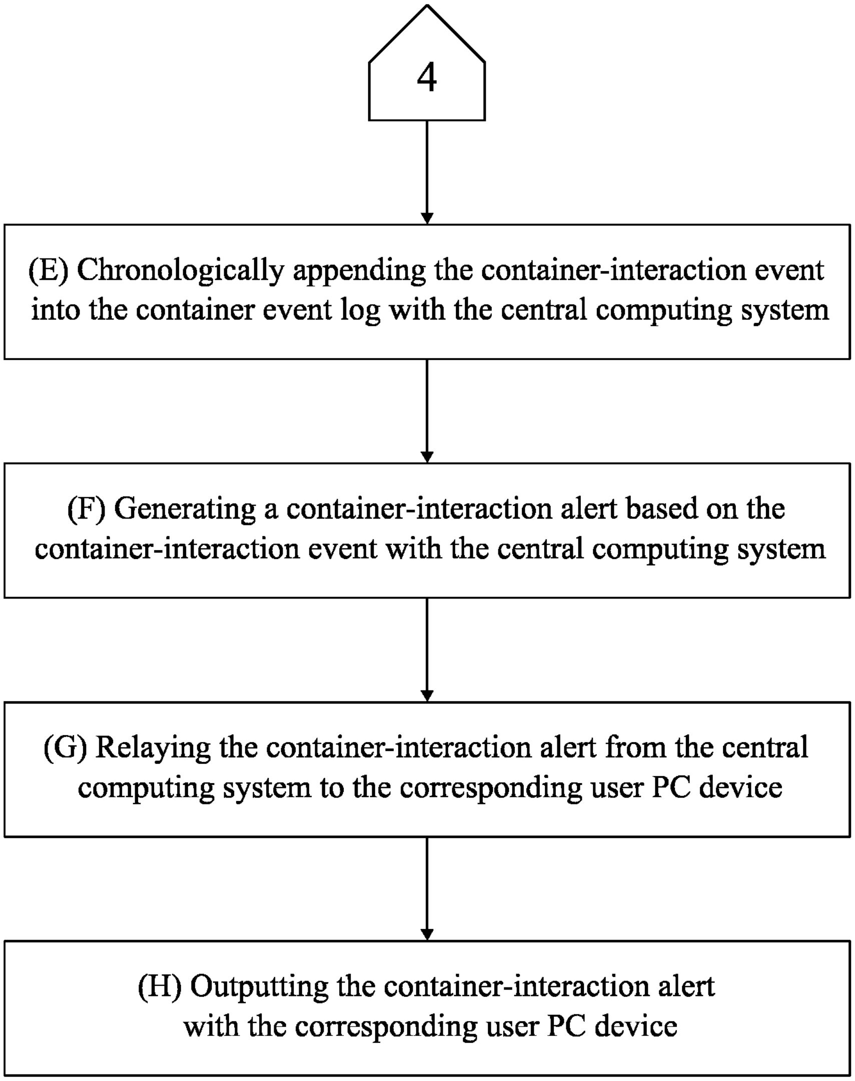
FIG. 5 is a flowchart depicting the continuation of the overall process of the present invention.

The overall process followed by the method of the present invention enables the automatic and efficient monitoring and control of medication consumption of any user. As can be seen in FIGS. 4 and 5, the system further includes at least one user account and at least one container event log managed by at least one central computing system (Step B). The user account corresponds to the user authorized to monitor and control the computerized medication container 1. The authorized user can be a caregiver, nurse, or the same user taking the medication. The container event log includes data regarding physical events that are happening with the computerized medication container 1 that are recorded by the monitoring camera 3. Further, the user account is associated with the computerized medication container 1 and a corresponding user personal computing (PC) device. The corresponding user PC device can be any computing device with wireless connectivity that enables the transmission of data to/from the central computing system. The corresponding user PC device can be but is not limited to, a smartphone, a tablet computer, a desktop computer, a laptop, etc. Further, any wireless communication protocol can be utilized to enable the wireless transmission of data including, but not limited to, short-distance wireless protocols such as Wi-Fi or Bluetooth or long-distance wireless protocols such as cellphone networks. Further, the container event log is associated with the computerized medication container 1. In other words, the computerized medication container 1 has a corresponding container event log for the physical events related to the container that can be related to medication utilization for case measurement and reporting. If the authorized user has access to several computerized medication containers, each computerized medication container 1 has a container event log so that the authorized user can audit and monitor each individual container. Furthermore, a corresponding software application can be provided to help the authorized users access relevant data of the computerized medication container 1. The software application can be developed for specific computing devices, such as a mobile application, desktop application, etc., and can include different features to access and edit the relevant data. Further, the software application can include means to interact with third-party software such as search engines or databases or can be developed to be used with third-party software in the form of a website, widget, etc. Furthermore, all processes performed by the present invention can be performed locally with the processor 2. Any resulting data can also be stored locally with a storage device provided with the computerized medication container 1.

As can be seen in FIGS. 4 and 5, the overall process continues by recording a container-interaction event with the monitoring camera 3, if the mechanical switch 4 is actuated by the computerized medication container 1 being in a physically-opened configuration (Step C). In other words, when the user opens the computerized medication container 1, such as opening a lid or door of the computerized medication container 1, the mechanical switch 4 is actuated, and the action is processed by the processor 2 as a container-interaction event. However, the container-interaction event can include other occurrences including, but not limited to, the user coming close to the computerized medication container 1, the user accessing an already opened computerized medication container 1, the user configuring the computerized medication container 1 using the user interface 6, etc. Once the container-interaction event is detected by the processor 2, the monitoring camera 3 is activated to record the surroundings of the computerized medication container 1. The physically-opened configuration preferably corresponds to the configuration where the door, opening, or lid of the computerized medication container 1 is opened and allow access into the computerized medication container 1. Further, the mechanical switch 4 can be configured to be actuated when the computerized medication container 1 is opened. For example, the mechanical switch 4 can be a normally closed switch that is disengaged when the user opens the door, opening, or lid of the computerized medication container 1. The mechanical switch 4 can also be a normally open switch that is engaged when the user opens the door, opening, or lid of the computerized medication container 1.

As can be seen in FIGS. 4 and 5, after the container-interaction event occurs, the container-interaction event is relayed from the monitoring camera 3, through the processor 2, and to the central computing system, if the container-interaction event is recorded by the monitoring camera 3 (Step D). The recording of the container-interaction event is relayed to the central computing system for auditing purposes and for further processing. Once the container-interaction event is relayed to the central computing system, the container-interaction event is chronologically appended into the container event log with the central computing system (Step E). The authorized user can audit the container event log for different purposes, such as auditing the medication access history, the medication usage or non-usage history, as well as to check the system status of the computerized medication container 1. The recording of the container-interaction event can also be used to notify the authorized users of whenever the event occurs. A container-interaction alert is generated based on the container-interaction event with the central computing system (Step F). The container-interaction alert helps the authorized users to keep track of when the computerized medication container 1 has been opened. To do so, the container-interaction alert is relayed from the central computing system to the corresponding user PC device (Step G). Then, the container-interaction alert is outputted with the corresponding user PC device (Step H). For example, if the authorized user is utilizing a smartphone, the container-interaction alert can be displayed as a push notification. This way, authorized users can keep track of when the medication is being taken.

Figure 6:
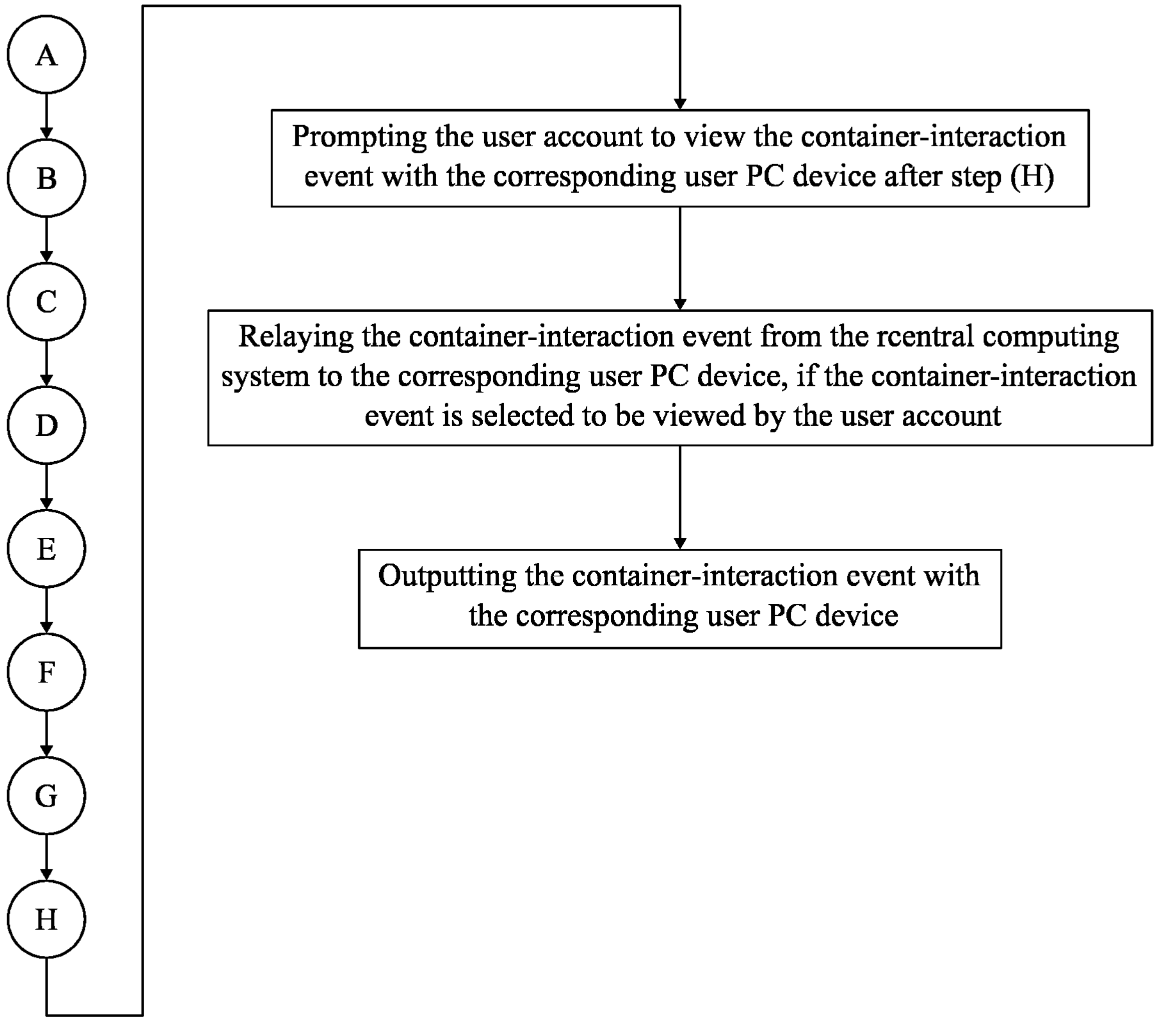
FIG. 6 is a flowchart depicting the subprocess of enabling authorized users to monitor the container-interaction event in real-time.

The present invention can enable the authorized users to monitor the interactions of other users with the computerized medication container 1 on real-time. This enables authorized users to take immediate actions, if the user is improperly taking the medication, such as taking the medication at the wrong time, taking the wrong medication, or the wrong amount of the medication. As can be seen in FIG. 6, the subprocess of enabling authorized users to monitor the container-interaction event in real-time involves prompting the user account to view the container-interaction event with the corresponding user PC device after Step H. The corresponding software application on the corresponding user PC device can include a function that enables the user to select if the authorized user wants to watch the container-interaction event. The container-interaction event is relayed from the central computing system to the corresponding user PC device, if the container-interaction event is selected to be viewed by the user account. Then, the container-interaction event is outputted with the corresponding user PC device. Different data corresponding to the container-interaction event can be relayed to the corresponding user PC device and outputted by the corresponding user PC device depending on the capabilities of the corresponding user PC device. For example, if the corresponding user PC device can display videos, the recording of the container-interaction event can be played by the corresponding user PC device. In other embodiments, different container-interaction event data can be relayed and outputted by the corresponding user PC device, such as a text summary of the container-interaction event, an audio recording, a text transcription, etc.

Figure 7:
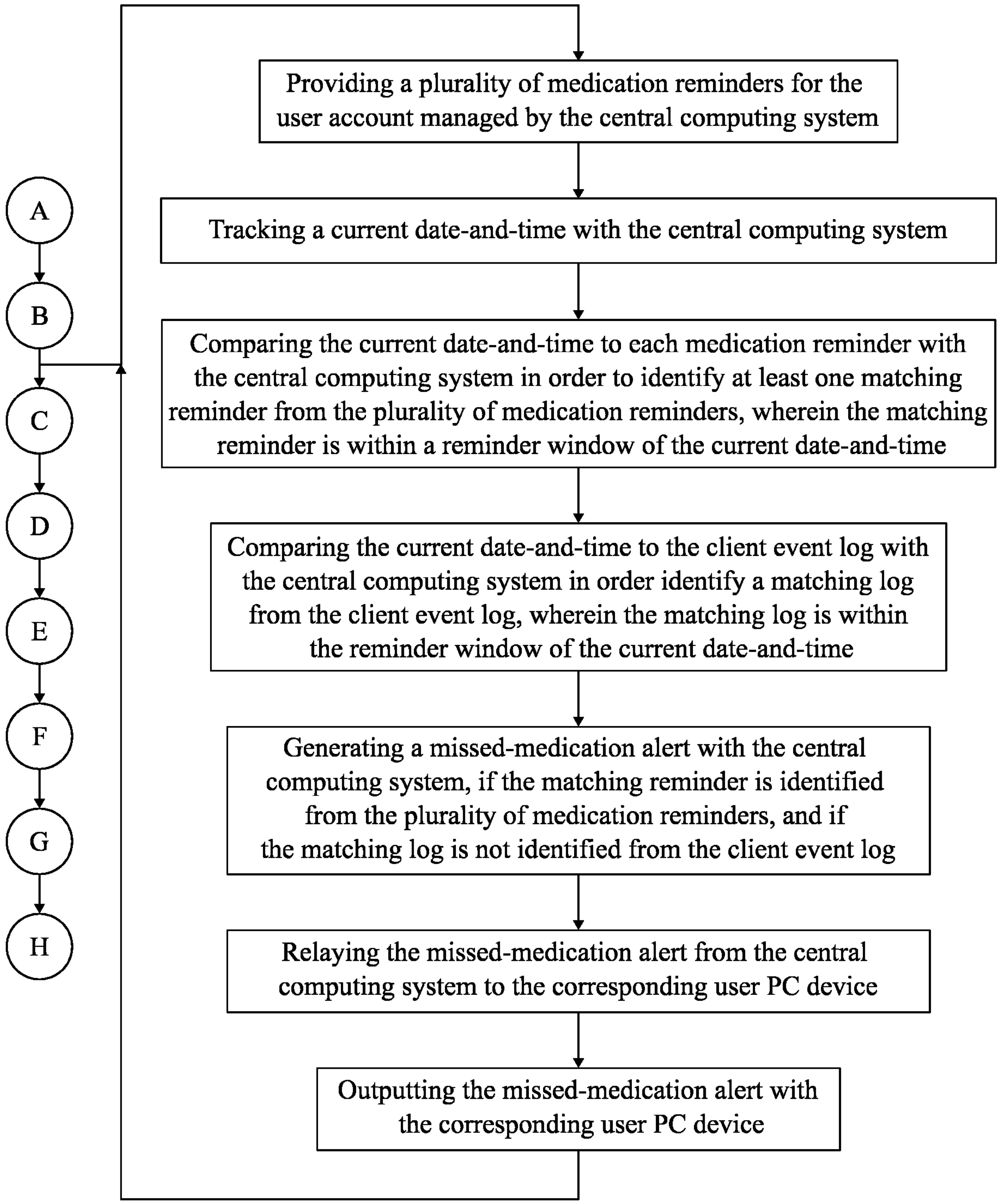
FIG. 7 is a flowchart depicting the subprocess of alerting the authorized user of medication reminders.

In addition to helping authorized users monitor the medication consumption of a user, the present invention also helps the authorized user to control when the user medication consumption. To do so, a plurality of medication reminders is provided for the user account managed by the central computing system. The plurality of medication reminders can include several reminders such as reminders to take the medication, reminders about the proper way to take the medication, reminders to refill the medication, etc. As can be seen in FIG. 7, the subprocess of alerting the authorized user of medication reminders involves tracking a current date-and-time with the central computing system. The date and time can be configured to match the location and corresponding time zone of the user. Then, the current date-and-time is compared to each medication reminder with the central computing system in order to identify at least one matching reminder from the plurality of medication reminders, wherein the matching reminder is within a reminder window of the current date-and-time. In other words, the central computing system can store several reminders that the authorized user has setup or are preconfigured by a service provider. The central computing system keeps track of the several reminders and identifies the reminders that are due according to the preset date and time when the authorized is supposed to be alerted of the reminders. In addition, the current date-and-time is compared to the client event log with the central computing system in order identify a matching log from the client event log, wherein the matching log is within the reminder window of the current date-and-time. This enables certain reminders to be correctly relayed to the authorized user depending on the user's interactions with the computerized medication container 1. For example, if the authorized user sets a reminder to take a certain medication, the system can check if the user has taken the medication at the preset time and alert the user accordingly. If the user has taken the medication, the reminder is not processed. However, a missed-medication alert is generated with the central computing system, if the matching reminder is identified from the plurality of medication reminders, and if the matching log is not identified from the client event log. In other words, the missed-medication alert is generated if no container-interaction event occurred during the corresponding date and time. The missed-medication alert is relayed from the central computing system to the corresponding user PC device. Then, the missed-medication alert is outputted with the corresponding user PC device. This way, the authorized users can keep track of the user's medication consumption habits and take the necessary actions, if the user is not taking the medication properly. In other embodiments, additional alerts can be generated such as medication refill reminders, system update reminders, etc.

Figure 8:
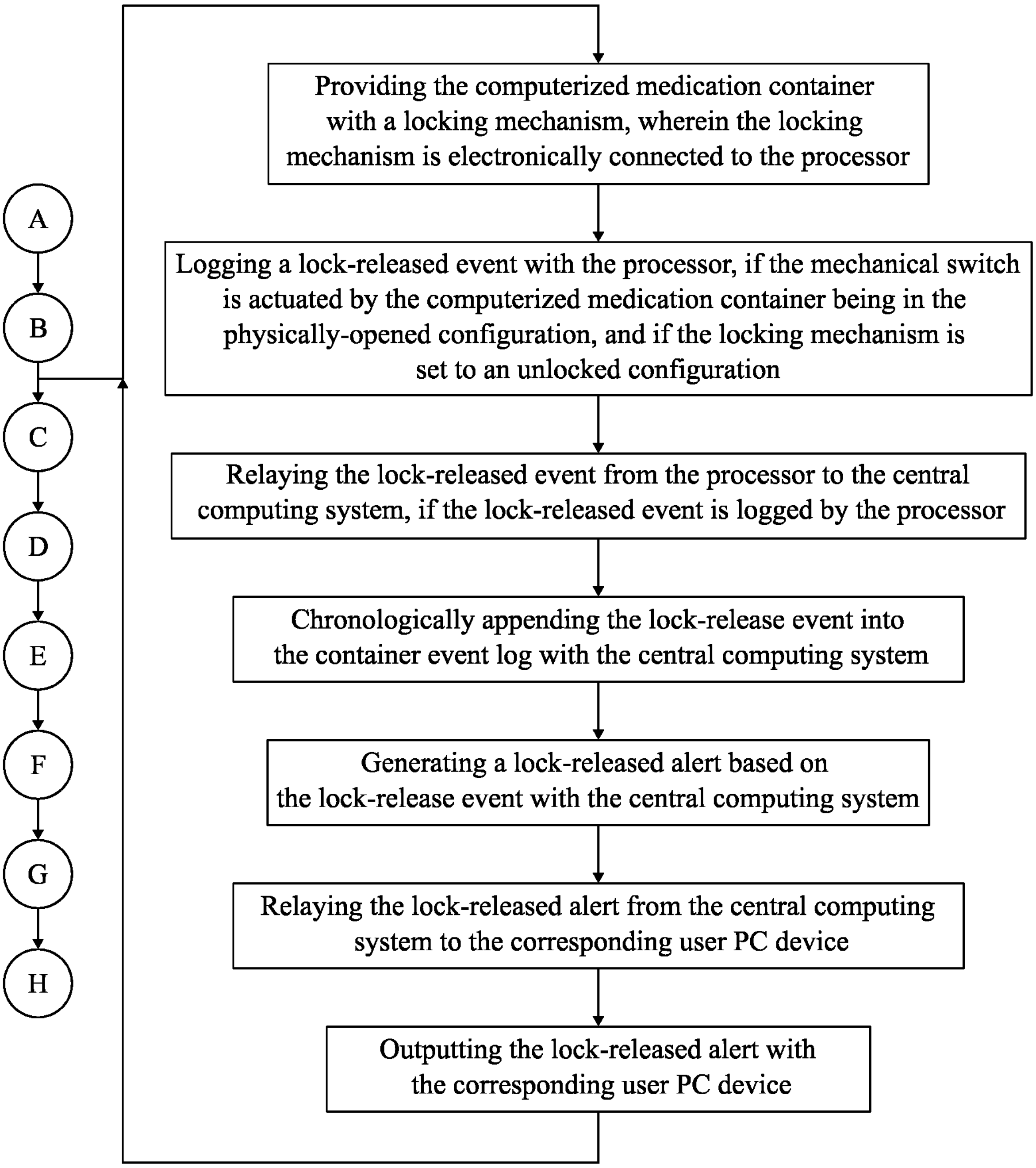
FIG. 8 is a flowchart depicting the subprocess of tracking when the locking mechanism has been unlocked.

As previously discussed, the present invention securely stores the desired medication. To do so, the computerized medication container 1 can be provided with a locking mechanism. The locking mechanism can further prevent unauthorized access to the stored medication. For example, the locking mechanism can be used to keep children from consuming dangerous medications. The locking mechanism can include different mechanical, electrical, or electronic locks including, but not limited to, a combination lock, key lock, keypad, key fob, biometrical lock, etc. Further, the locking mechanism is electronically connected to the processor 2 so that necessary data can be collected for different processes, such as detecting when the locking mechanism has been unlocked, who has unlocked the locking mechanism, etc. As can be seen in FIG. 8, the subprocess of tracking when the locking mechanism has been unlocked involves logging a lock-released event with the processor 2, if the mechanical switch 4 is actuated by the computerized medication container 1 being in the physically-opened configuration, and if the locking mechanism is set to an unlocked configuration. In other words, the lock-released event occurs when the user unlocks the locking mechanism and opens the computerized medication container 1. The lock-released event is then relayed from the processor 2 to the central computing system, if the lock-released event is logged by the processor 2. The lock-released event can be used for auditing purposes such as determining who opened the computerized medication container 1 or who tried to open the computerized medication container 1, if the computerized medication container 1 was unlocked but not opened. Further, the lock-release event is chronologically appended into the container event log with the central computing system to keep secure and accurate records. In addition, a lock-released alert is generated based on the lock-release event with the central computing system. The lock-released alert can be combined with the container-interaction event if the computerized medication container 1 is unlocked and opened. However, the lock-released alert can be relayed individually from the central computing system to the corresponding user PC device if the computerized medication container 1 was only unlocked. Then, the lock-released alert is outputted with the corresponding user PC device to notify the authorized user when the computerized medication container 1 has been unlocked. In other embodiments, the lock-released alert can also include the identity of the user who unlocks the computerized medication container 1 if the locking mechanism includes means to identify the user such as when the locking mechanism utilizes individual key fobs are used by different users or when the locking mechanism captures biometric data. Further, the present invention can generate alerts to the authorized user when access has been successfully granted to the user.

Figure 9:
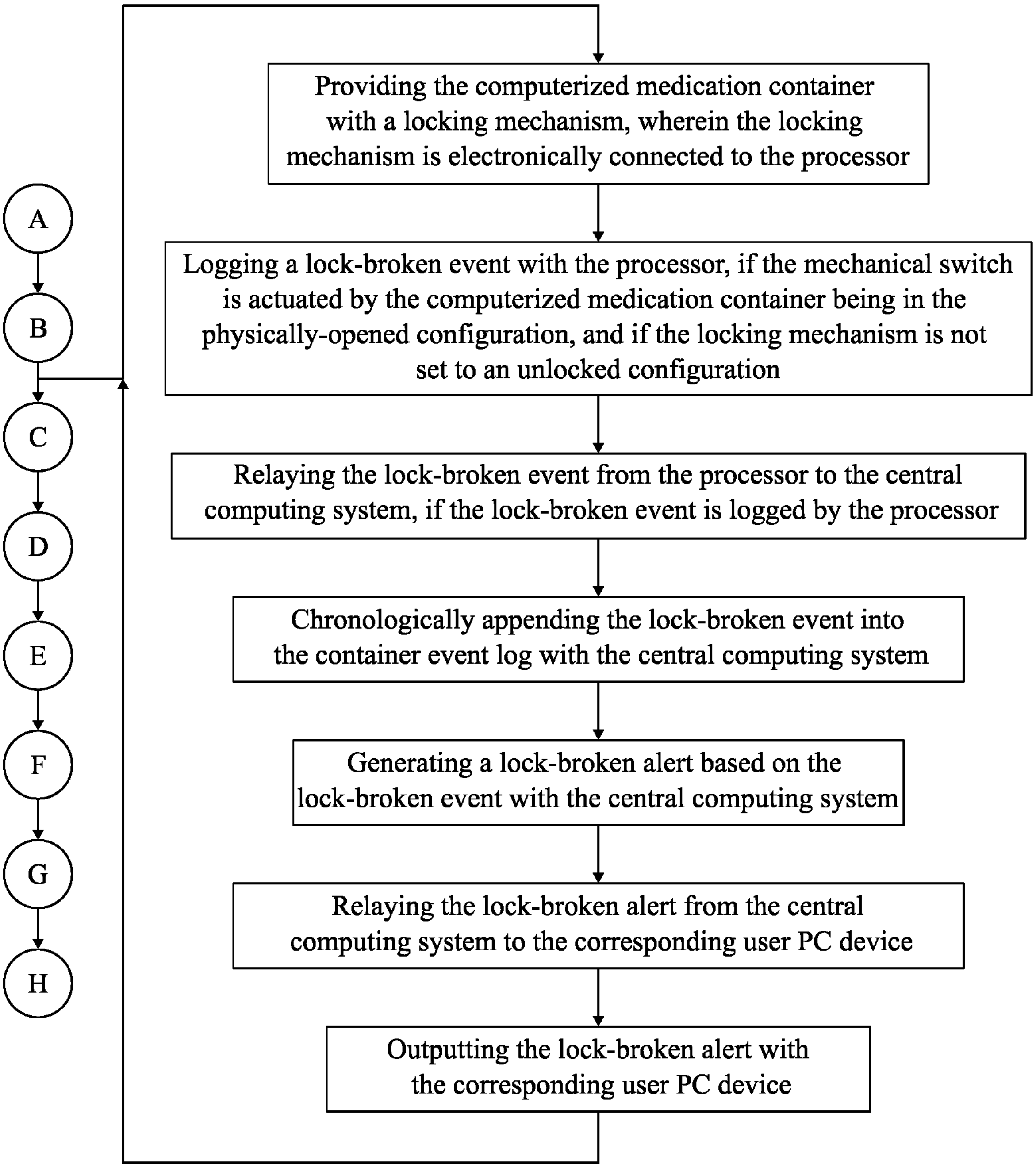
FIG. 9 is a flowchart depicting the subprocess of subprocess of alerting the authorized users of unauthorized access to the computerized medication container.

In addition to tracking when the computerized medication container 1 has been unlocked, the present invention can also notify users when the computerized medication container 1 has been tampered with or broken into. As can be seen in FIG. 9, the subprocess of alerting the authorized users of unauthorized access to the computerized medication container 1 involves logging a lock-broken event with the processor 2, if the mechanical switch 4 is actuated by the computerized medication container 1 being in the physically-opened configuration, and if the locking mechanism is not set to an unlocked configuration. In other words, the lock-broken event occurs when a user breaks into the computerized medication container 1 without properly unlocking the computerized medication container 1. The lock-broken event is relayed from the processor 2 to the central computing system, if the lock-broken event is logged by the processor 2. Then, the lock-broken event is chronologically appended into the container event log with the central computing system to keep a safe record of the lock-broken event. A lock-broken alert is generated based on the lock-broken event with the central computing system, which is then relayed from the central computing system to the corresponding user PC device. Then, the lock-broken alert is outputted with the corresponding user PC device. This way, the authorized user is promptly alerted of unauthorized access to the computerized medication container 1 so that the authorized user can take the proper actions.

Figure 10:
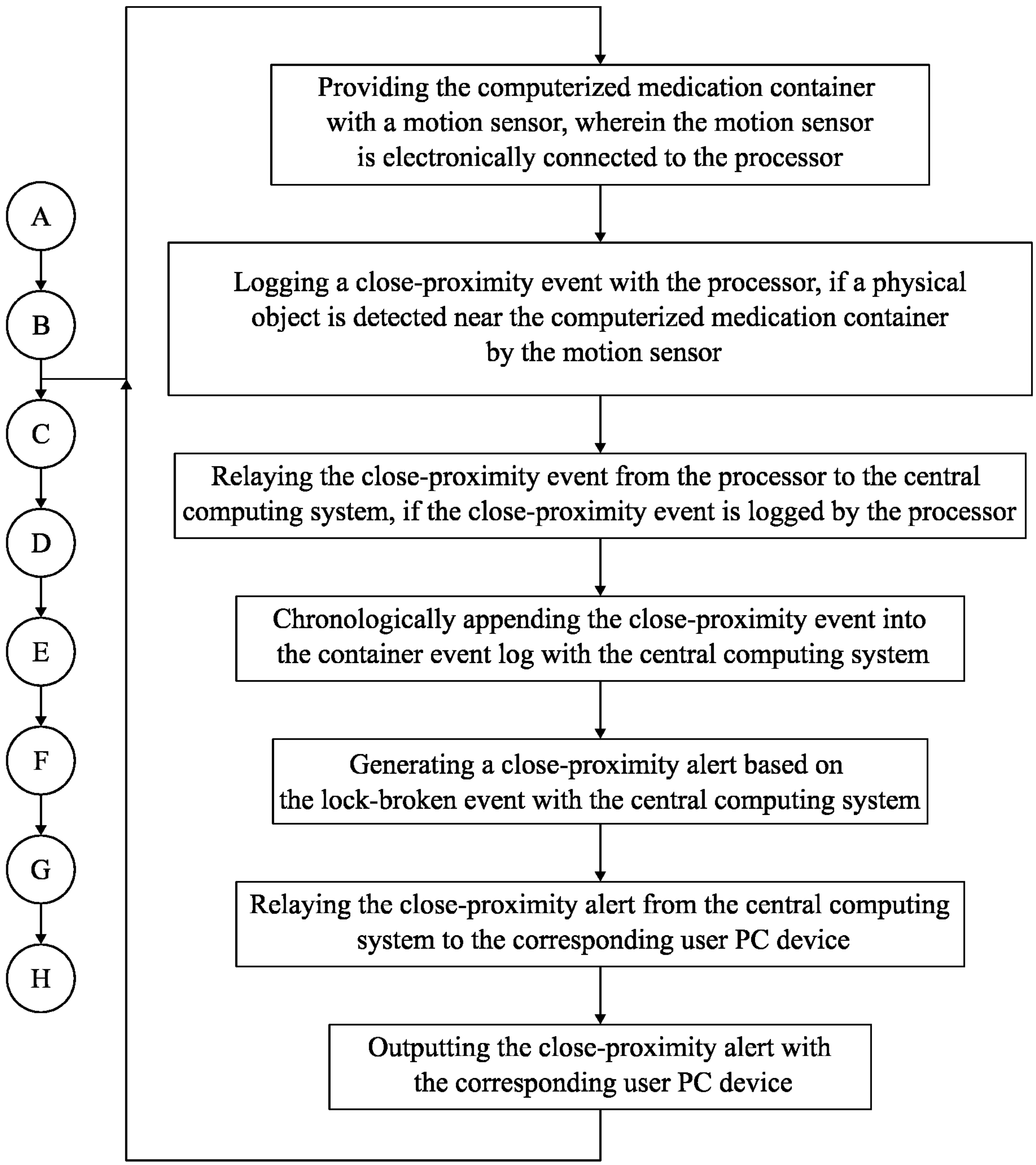
FIG. 10 is a flowchart depicting the subprocess of tracking the user motion around the computerized medication container.

In addition to the locking mechanism, the present invention can include other means to monitor the surroundings of the computerized medication container 1. To do so, the computerized medication container 1 can be provided with a motion sensor. The motion sensor provides additional security to the computerized medication container 1 by enabling the tracking of user movements around the computerized medication container 1. The motion sensor is electronically connected to the processor 2 to enable the transmission of sensor signals to the processor 2. As can be seen in FIG. 10, the subprocess of tracking the user motion around the computerized medication container 1 involves logging a close-proximity event with the processor 2, if a physical object is detected near the computerized medication container 1 by the motion sensor. In other words, the close-proximity event occurs when the motion sensor detects movement around the computerized medication container 1. The close-proximity event is relayed from the processor 2 to the central computing system, if the close-proximity event is logged by the processor 2. Then, the close-proximity event is chronologically appended into the container event log with the central computing system for safe records. A close-proximity alert is generated based on the close-proximity event with the central computing system. For example, the close-proximity alert can be configured to be generated if a distance threshold between the user and the computerized medication container 1 is detected. Then, the close-proximity alert is relayed from the central computing system to the corresponding user PC device, which is then outputted with the corresponding user PC device. This way, the authorized users can keep track of who goes close the computerized medication container 1 to better control access to the stored medication. The motion sensor can also be used along with the mechanical switch 4 to prompt the recording of the container-interaction event if the mechanical switch 4 fails to be actuated but the motion sensor does detect close proximity of the user to the computerized medication container 1.

Figure 11:
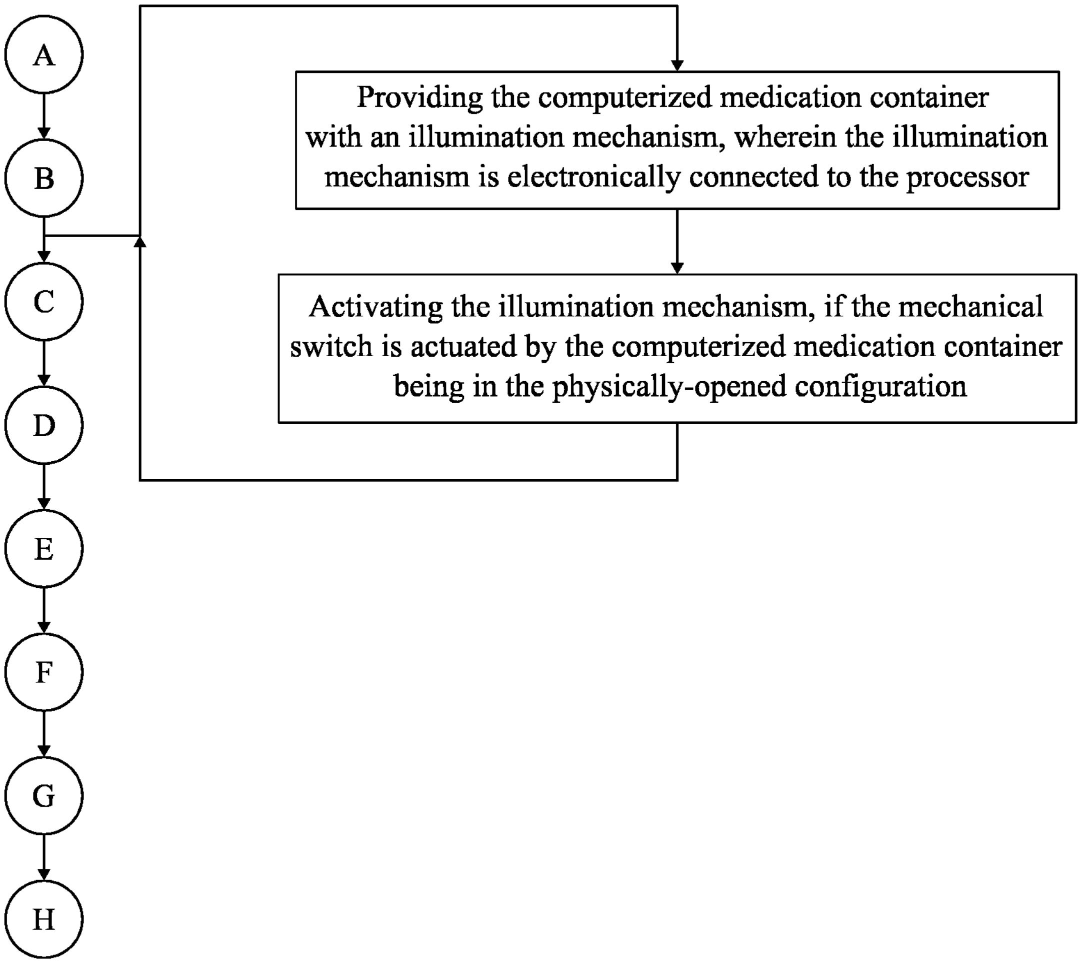
FIG. 11 is a flowchart depicting the subprocess of automatically activating the illumination mechanism.

To further facilitate the user to take the medication as well as to facilitate the recording of the container-interaction event, the computerized medication container 1 can be provided with an illumination mechanism 5. The illumination mechanism 5 helps illuminate the surroundings of the computerized medication container 1 to help guide the user to the computerized medication container 1 as well as to improve the recording quality of the container-interaction event. The illumination mechanism 5 is electronically connected to the processor 2 to enable the automatic activation of the illumination mechanism 5 at the correct situations. As can be seen in FIG. 11, the subprocess of automatically activating the illumination mechanism 5 involves activating the illumination mechanism 5, if the mechanical switch 4 is actuated by the computerized medication container 1 being in the physically-opened configuration. In other words, the illumination mechanism 5 is activated when the computerized medication container 1 has been opened by the user. In case the mechanical switch 4 fails to be actuated, the illumination mechanism 5 can also be activated when the motion sensor detects close proximity of a user to the computerized medication container 1, or when the locking mechanism has been unlocked. Furthermore, the illumination mechanism can be directly activated from the user interface 6 as the user desires.

Figure 12:
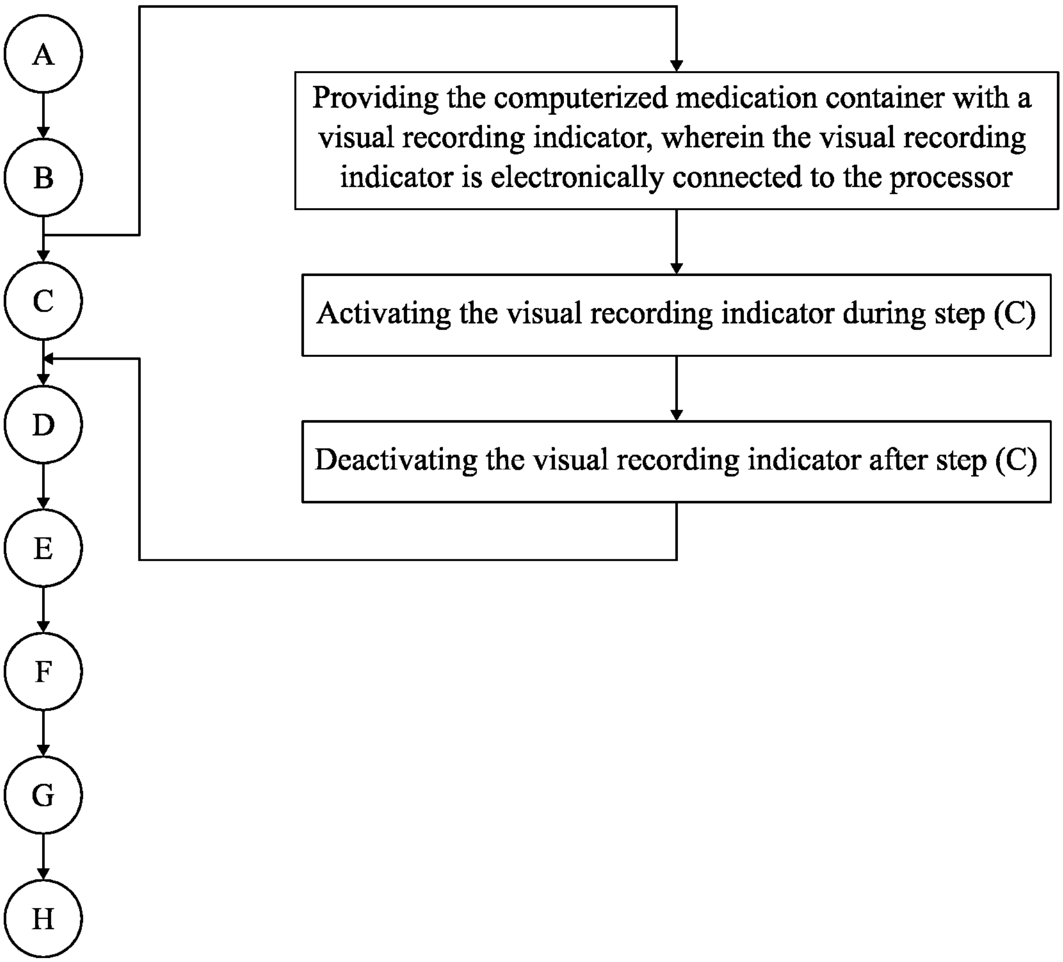
FIG. 12 is a flowchart depicting the subprocess of alerting the user of the recording during the container-interaction event.

To further protect the privacy of the user, the present invention can notify the user when the user is being recorded. To do so, the computerized medication container 1 can be provided with a visual recording indicator. The visual recording indicator can be a light source that is clearly visible by the user so that the user can be sure of when the user is being recorded. Further, the visual recording indicator is electronically connected to the processor 2 to enable the automatic activation of the recording indicator in the right situations. As can be seen in FIG. 12, the subprocess of alerting the user of the recording during the container-interaction event involves activating the visual recording indicator during Step C. This way, the user is alerted when the container-interaction event is being recorded. Then, the visual recording indicator is deactivated after Step C so that the user knows when the recording has finished. In other embodiments, additional indicators can be included to indicate the user of different events. Further, auditory indicators can also be utilized instead of or along with the visual recording indicator.

Figure 13:
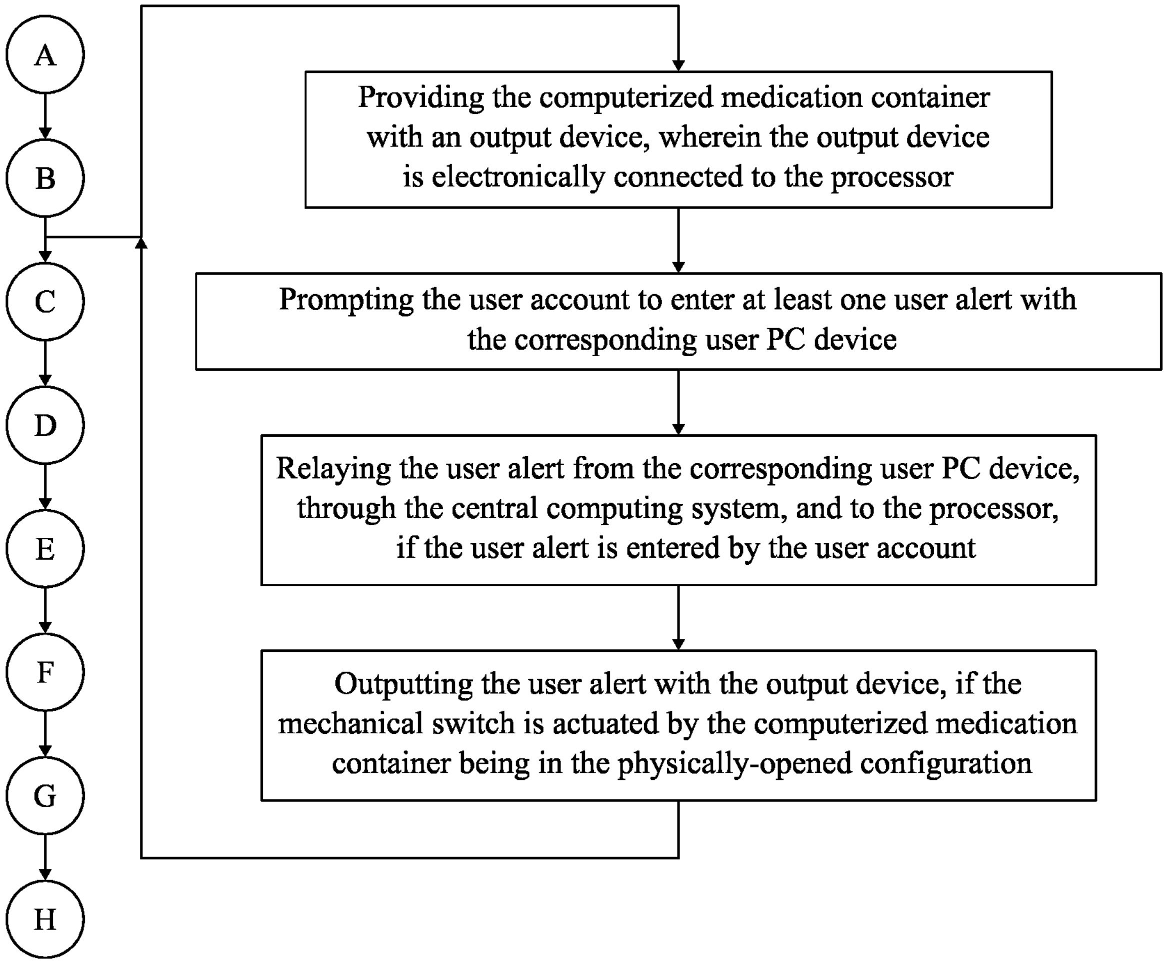
FIG. 13 is a flowchart depicting the subprocess of recording and outputting user alerts.

In addition to enabling the authorized users monitor and control the medication consumption, the present invention can also enable the authorized users to set alerts or reminders for the user when the user approaches the computerized medication container 1. To do so, the medication container is provided with an output device 7 such as a speaker or a user interface 6 that enables the output of visual or auditory alerts. The output device 7 is electronically connected to the processor 2 to enable the automatic output of the alerts or reminders in the proper situations. As can be seen in FIG. 13, the subprocess of recording and outputting user alerts involves prompting the user account to enter at least one user alert with the corresponding user PC device. The authorized users can set customized reminders or alerts such as reminding the user of taking specific medication or the right amount of any medication. The authorized users can also select preconfigured reminders or alerts provided on the corresponding software application. Then, the user alert is relayed from the corresponding user PC device, through the central computing system, and to the processor 2, if the user alert is entered by the user account. This way, the alert or reminder is stored in the computerized medication container 1 to be automatically outputted by the output device 7. Finally, the user alert is outputted with the output device 7, if the mechanical switch 4 is actuated by the computerized medication container 1 being in the physically-opened configuration. In other words, when the user opens the computerized medication container 1, the user alerts or reminders are outputted as configured. The user alerts or reminders can also be configured to be outputted at different situations, such as when a close proximity is detected by the motion sensor, or at a predetermined schedule. This way, the user is further helped to properly take the medication.

Figure 14:
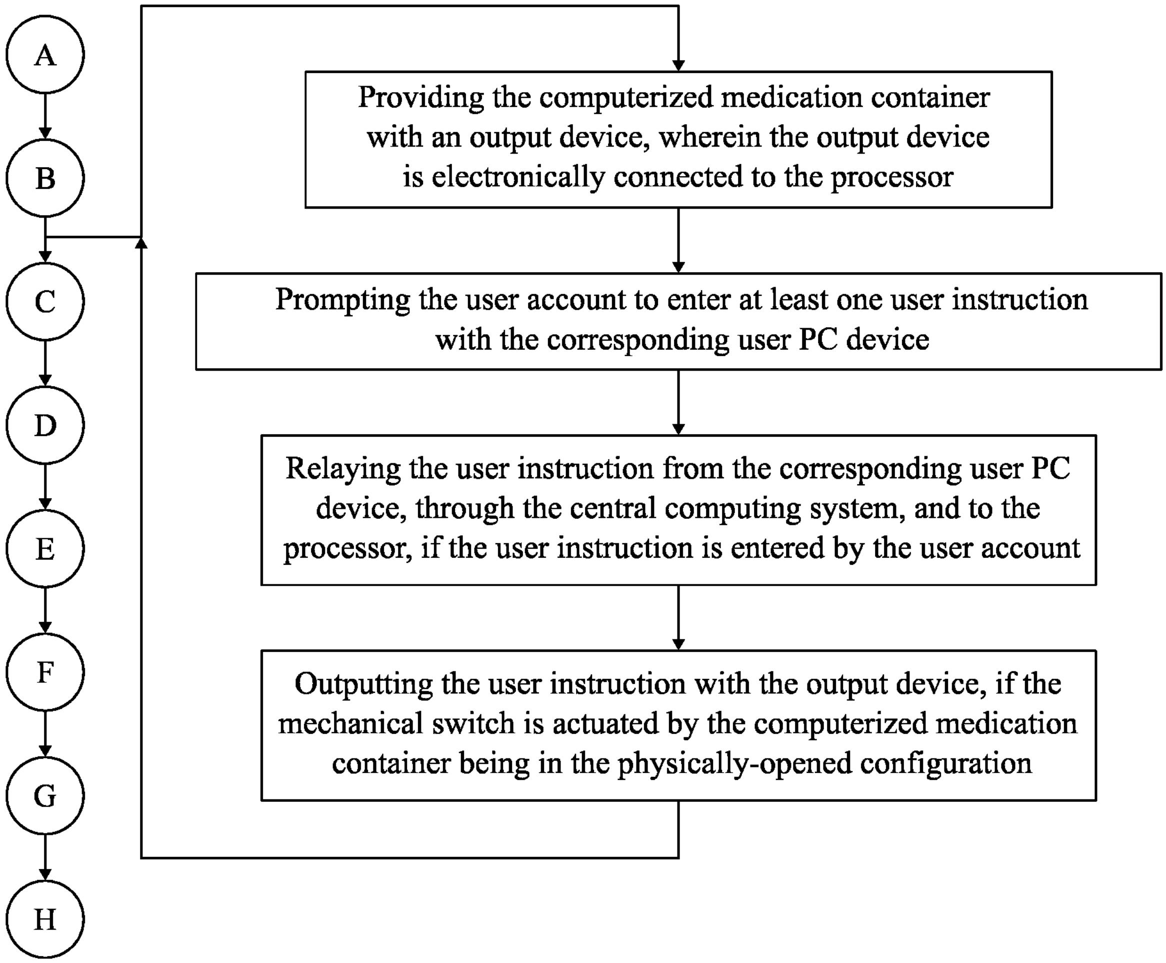
FIG. 14 is a flowchart depicting the subprocess of recording and outputting user instructions.

Similar to the user alerts, the present invention can also enable the authorized users to record instructions for the users to take the user's medications. As can be seen in FIG. 14, the subprocess of recording and outputting user instructions involves prompting the user account to enter at least one user instruction with the corresponding user PC device. The user instructions can include specific instructions of taking a medicine or to perform other actions while the user is engaging the computerized medication container 1. This is very helpful for parents who need to instruct children of how to take a medication when the parents are not present. The user instruction is relayed from the corresponding user PC device, through the central computing system, and to the processor 2, if the user instruction is entered by the user account. This way, the user instructions are stored in the computerized medication container 1 to be automatically outputted when appropriate. Finally, the user instruction is outputted with the output device 7, if the mechanical switch 4 is actuated by the computerized medication container 1 being in the physically-opened configuration. In other embodiments, the user instructions can be outputted at other different situations, such as when a close proximity is detected by the motion sensor, or at a predetermined schedule.

Figure 15:
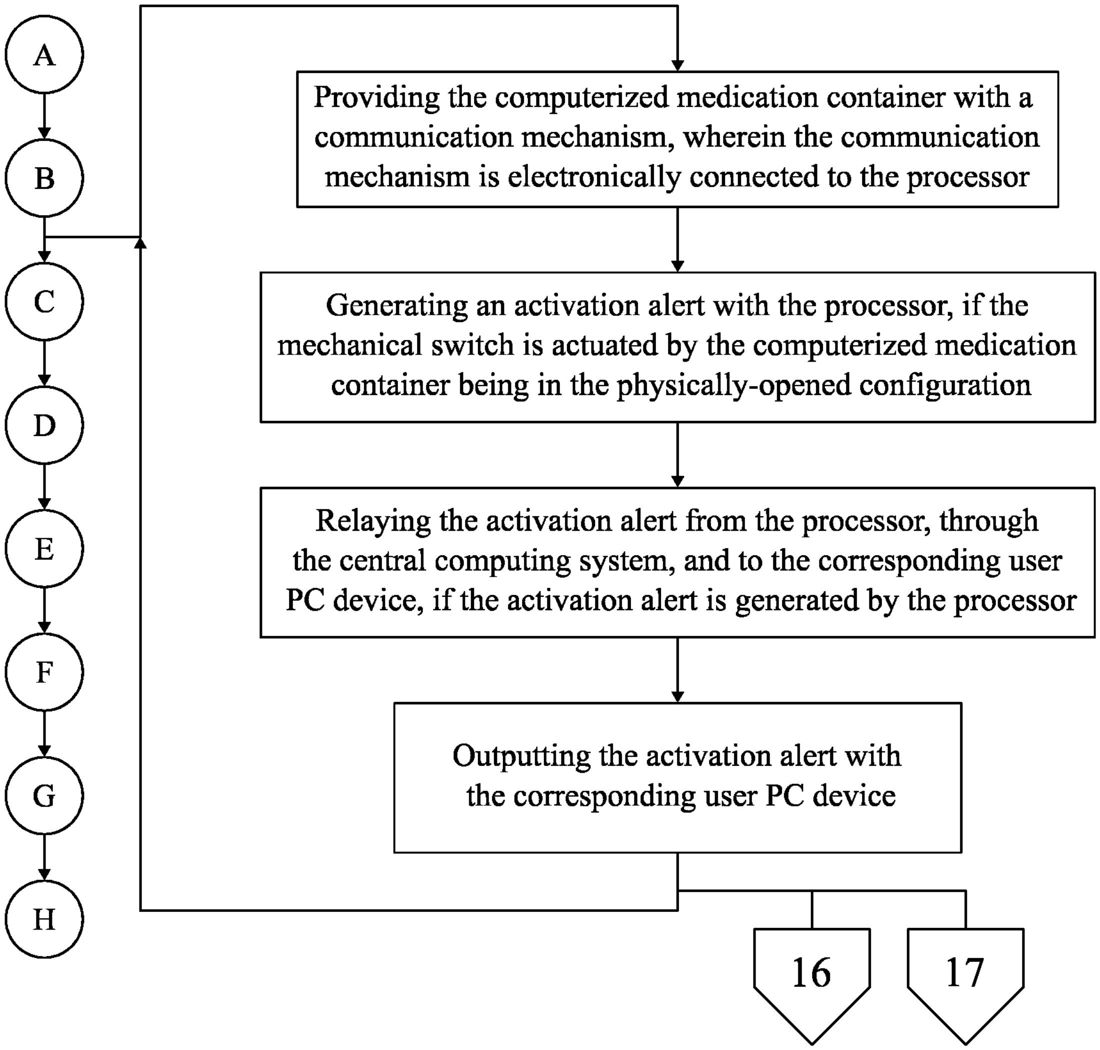
FIG. 15 is a flowchart depicting the subprocess of prompting the authorized user to provide user instructions in real time.

Furthermore, the present invention can also enable the authorized users to provide instructions for the users to take the user's medications in real time. To do so, the medication container is provided with a communication mechanism that enables the user to receive the user instruction in real time from an authorized user as well to respond to the authorized user if necessary. The communication mechanism includes the communication module 8 that enables the wireless communication between users via different wireless protocols including, but not limited to, cellular internet, two-way RF protocols, etc. The communication mechanism is electronically connected to the processor 2 to enable the transmission of user instructions in real time. As can be seen in FIG. 15, the subprocess of prompting the authorized user to provide user instructions in real time involves generating an activation alert with the processor 2, if the mechanical switch 4 is actuated by the computerized medication container 1 being in the physically-opened configuration. In other words, the authorized user is notified when the computerized medication container 1 is engaged by the user so that the authorized user can get ready to provide user instructions. The activation alert is relayed from the processor 2, through the central computing system, and to the corresponding user PC device, if the activation alert is generated by the processor 2. Then, the activation alert is outputted with the corresponding user PC device to notify the authorized user to start providing user instructions.

Figure 16:
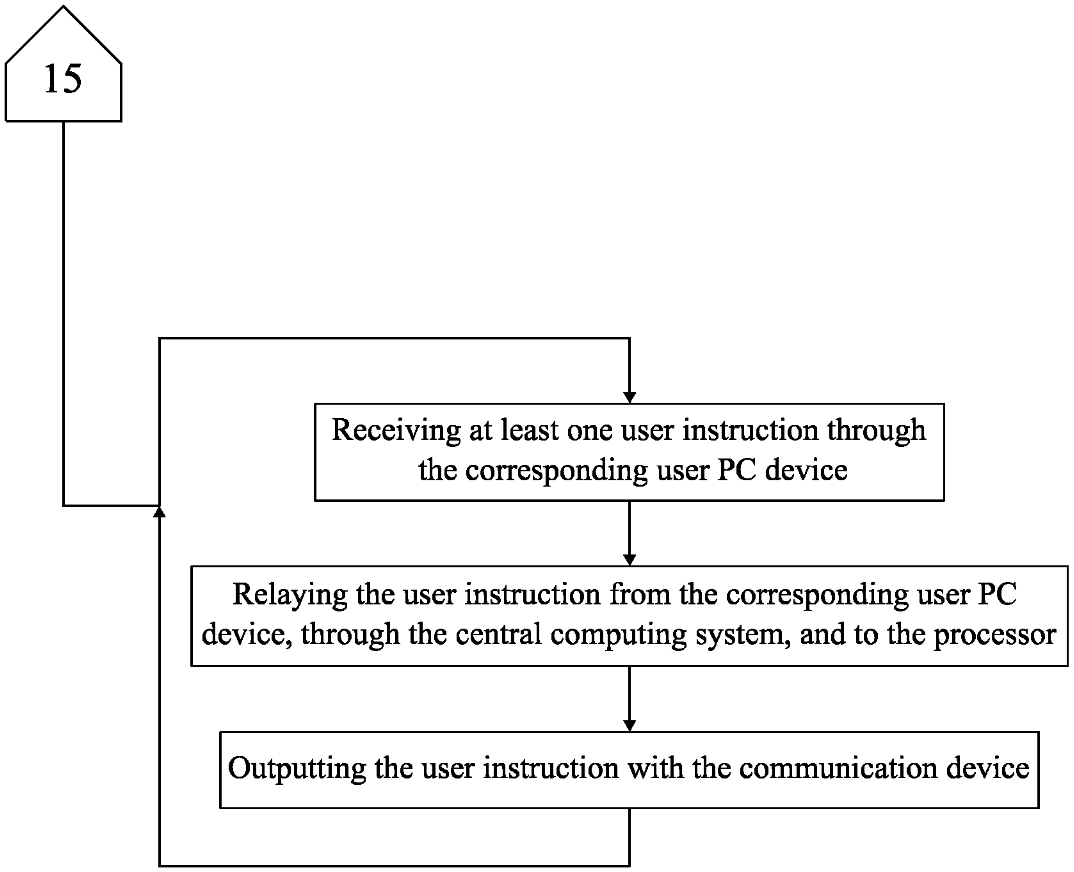
FIG. 16 is a flowchart depicting the subprocess of transmitting user instructions in real time.
Figure 17:
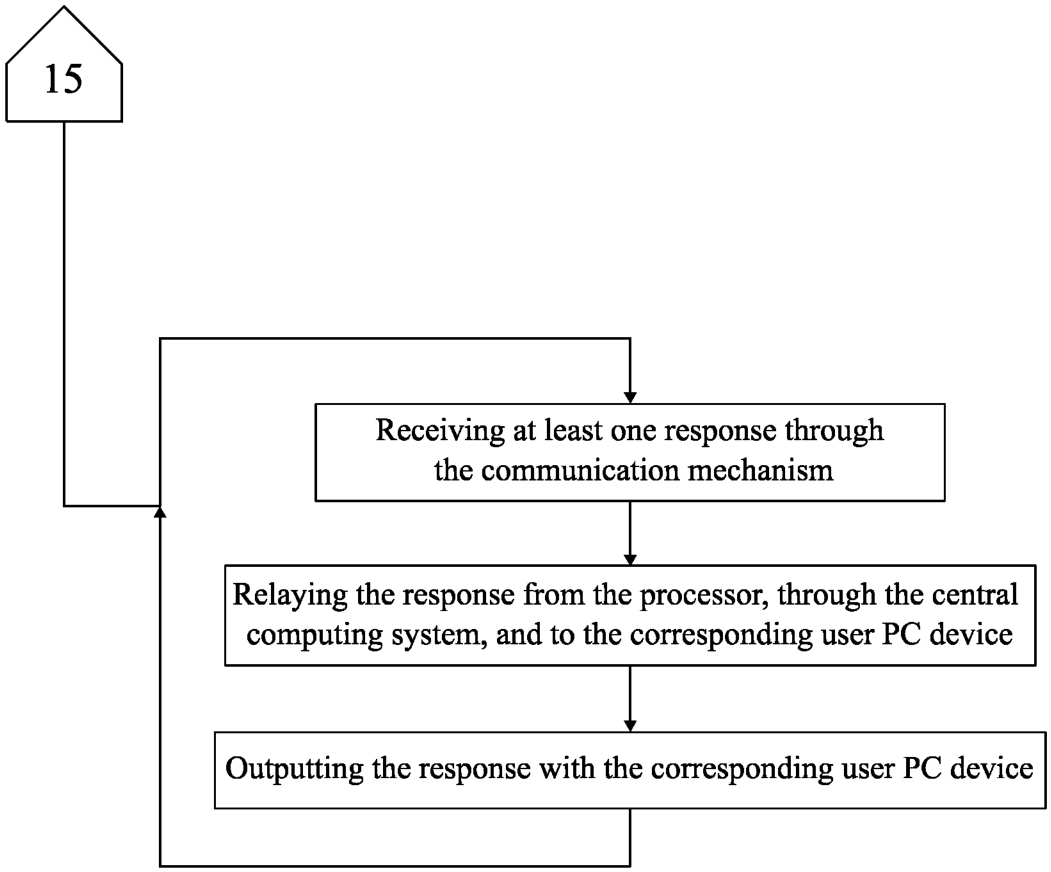
FIG. 17 is a flowchart depicting the subprocess of transmitting user responses.

Once the authorized user is ready to provide user instructions, the user instructions are relayed in real time to the user engaging the computerized medication container 1. As can be seen in FIG. 16, the subprocess of transmitting user instructions in real time involves receiving at least one user instruction through the corresponding user PC device from the authorized user. Then, the user instruction is relayed from the corresponding user PC device, through the central computing system, and to the processor 2. Further, the user instruction is outputted with the communication mechanism to provide the user with real time instructions. The subprocess continues while the user is taking the medication according to the user instructions. At the same time, the user can respond to the authorized user if necessary. As can be seen in FIG. 17, the subprocess of transmitting user responses involves receiving at least one response through the communication mechanism. The response can include questions, concerns, or anything the user wants to convey to the authorized user. The response is relayed from the processor 2, through the central computing system, and to the corresponding user PC device. Then, the response is outputted with the corresponding user PC device to the authorized user so that the authorized user can reply accordingly. The authorized user can stop these subprocesses after the user is done taking the medication using a corresponding function on the corresponding software application. Similarly, the user can stop these subprocesses via a user interface 6 provided on the computerized medication container 1.

Figure 18:
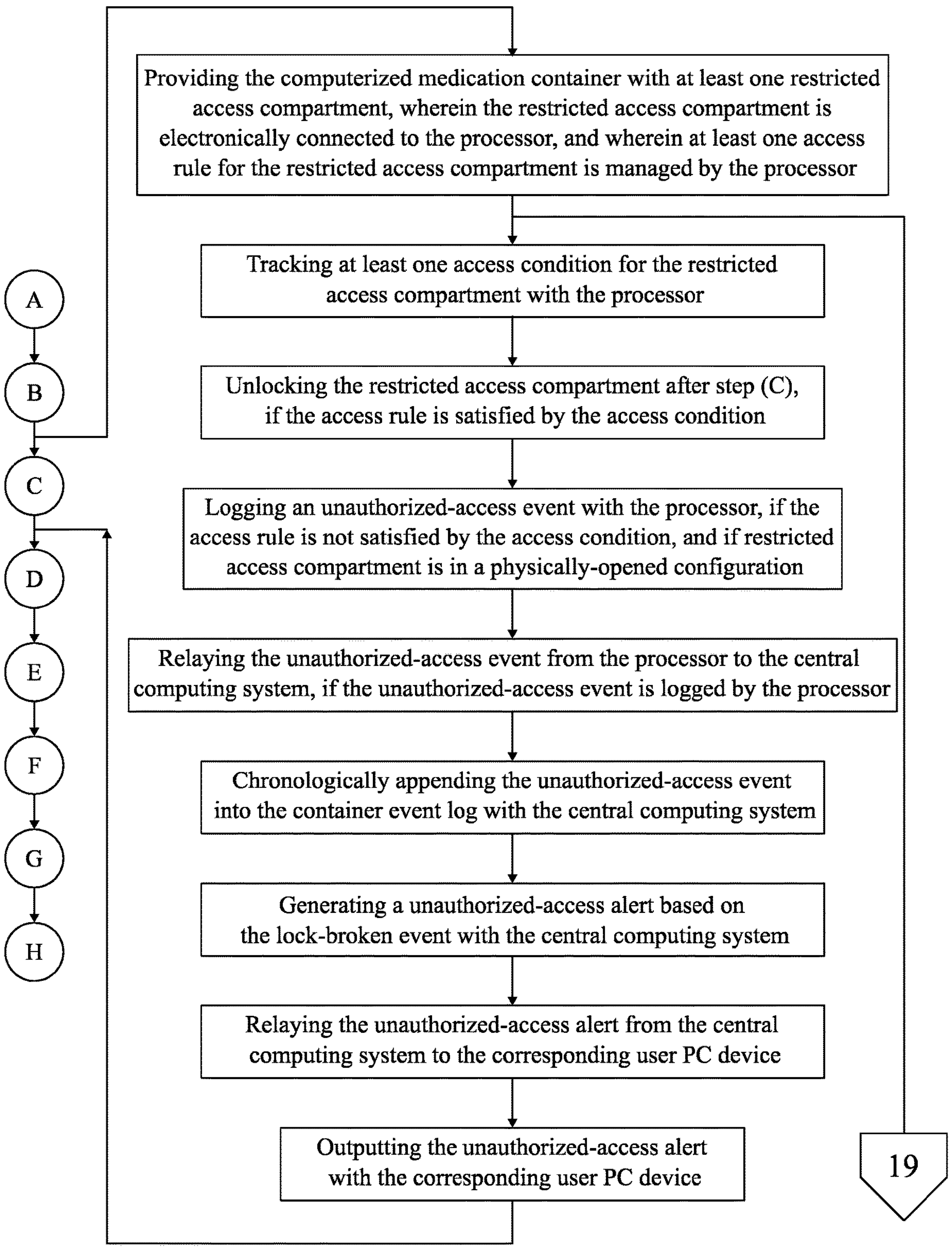
FIG. 18 is a flowchart depicting the subprocess of unlocking the restricted access compartment according to an access rule.

To further control the medication consumption, the present invention can provide additional security to specific stored medications so that these medications can only be taken at predetermined situations. For example, specific medications can be dispensed at specific times, to specific users, or after taking other medications. To do so, the medication container is provided with at least one restricted access compartment. The restricted access compartment allows different medications to be stored in the computerized medication container 1 while further controlling the consumption of the medications stored in the restricted access compartments. For example, medications for adults can be stored in the restricted access compartments, while children medication can be stored somewhere else in the computerized medication container 1. This enables access of both adult and children to the computerized medication container 1 while preventing children from taking adult medication. In addition, the restricted access compartment is electronically connected to the processor 2 for automatic unlocking of the restricted access compartment. Further, at least one access rule for the restricted access compartment is managed by the processor 2. The access rule helps dictate when the restricted access compartment can be accessed by the user, such as a predetermined schedule, specific users, etc. As can be seen in FIG. 18, the subprocess of unlocking the restricted access compartment according to the access rule involves tracking at least one access condition for the restricted access compartment with the processor 2. The access condition corresponds to the set access rule, such a time period the restricted access compartment can be accessed into, specific users opening the computerized medication container 1, etc. The restricted access compartment is unlocked after Step C, if the access rule is satisfied by the access condition. This way, the user can access the medication stored in the restricted access compartment only after the access rule is satisfied. Further, the present invention can generate notifications when the user has correct access to the medication stored in the restricted access compartment so that the authorized user can keep track of the user when the user is properly taking the medication.

As can be seen in FIG. 18, in the situations where the access rule is not satisfied, the authorized users are alerted accordingly. An unauthorized-access event is logged with the processor 2, if the access rule is not satisfied by the access condition, and if restricted access compartment is in a physically-opened configuration. In other words, if the user takes the medication from the restricted access compartment without following the access rule, the unauthorized-access event is recorded. Then, the unauthorized-access event is relayed from the processor 2 to the central computing system, if the unauthorized-access event is logged by the processor 2. In addition, the unauthorized-access event is chronologically appended into the container event log with the central computing system to maintain accurate records for auditing purposes. Then, an unauthorized-access alert is generated based on the unauthorized-access event with the central computing system, which is then relayed from the central computing system to the corresponding user PC device. Further, the unauthorized-access alert is outputted with the corresponding user PC device to alert the authorized users of the unauthorized access into the restricted access compartment.

Figure 19:
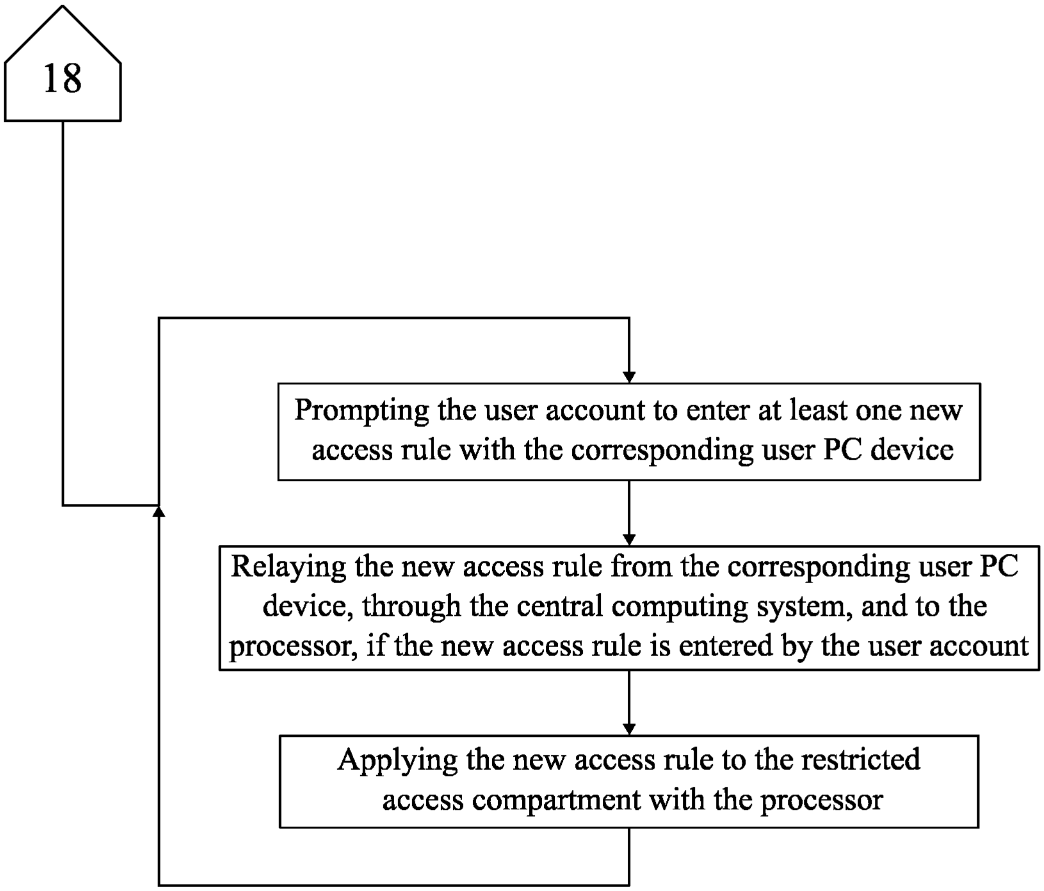
FIG. 19 is a flowchart depicting the subprocess of setting new access rules.

Furthermore, the present invention enables the authorized users to set custom access rules for each of the restricted access compartments. The authorized users can do so from the corresponding software application utilizing the appropriate functions. As can be seen in FIG. 19, the subprocess of setting new access rules involves prompting the user account to enter at least one new access rule with the corresponding user PC device. The new access rules can include setting a new schedule, giving access to new users, etc. The new access rule is relayed from the corresponding user PC device, through the central computing system, and to the processor 2, if the new access rule is entered by the user account. Then, the new access rule is applied to the restricted access compartment with the processor 2 so that the processor 2 can track the new rule conditions and grant access to the restricted access compartments accordingly.

Figure 20:
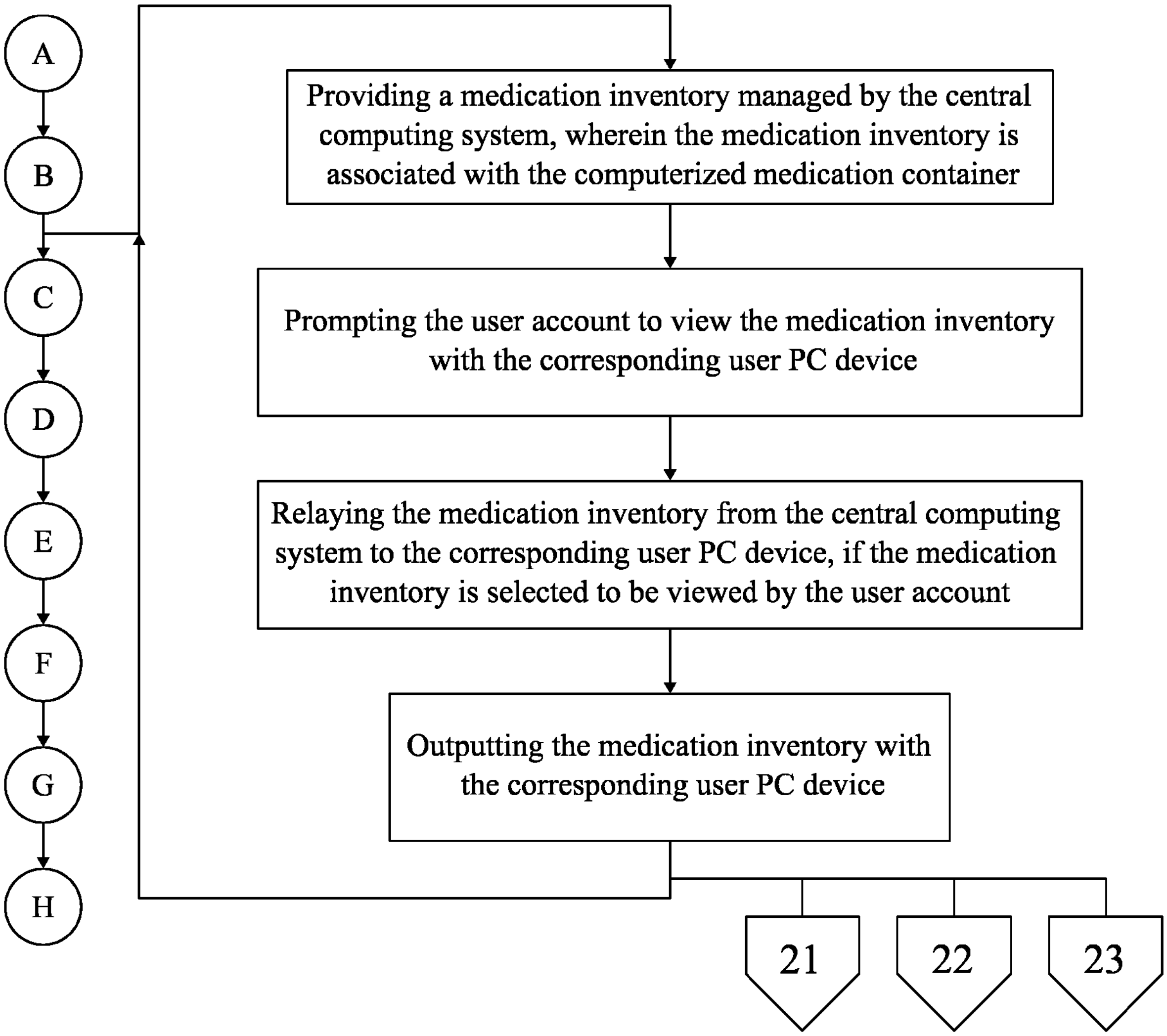
FIG. 20 is a flowchart depicting the subprocess of enabling the auditing of a medication inventory.

In addition to facilitating the monitoring and control of medication consumption by the users, the present invention can also facilitate the authorized users to keep track of the medication inventory in the computerized medication container 1. To do so, a medication inventory is provided that is managed by the central computing system. The medication inventory maintains a record of the medication stored within a computerized medication container 1. In addition, the medication inventory is associated with the computerized medication container 1, which enables authorized users to keep track of several medication inventories corresponding to different computerized medication containers. As can be seen in FIG. 20, the subprocess of enabling the auditing of a medication inventory involves prompting the user account to view the medication inventory with the corresponding user PC device. The authorized users can view the medication inventory via the corresponding software application by utilizing the appropriate functions. Further, the medication inventory is relayed from the central computing system to the corresponding user PC device, if the medication inventory is selected to be viewed by the user account. Then, the medication inventory is outputted with the corresponding user PC device to enable the authorized users to keep track of the medication inventory of a computerized medication container 1.

Figure 21:
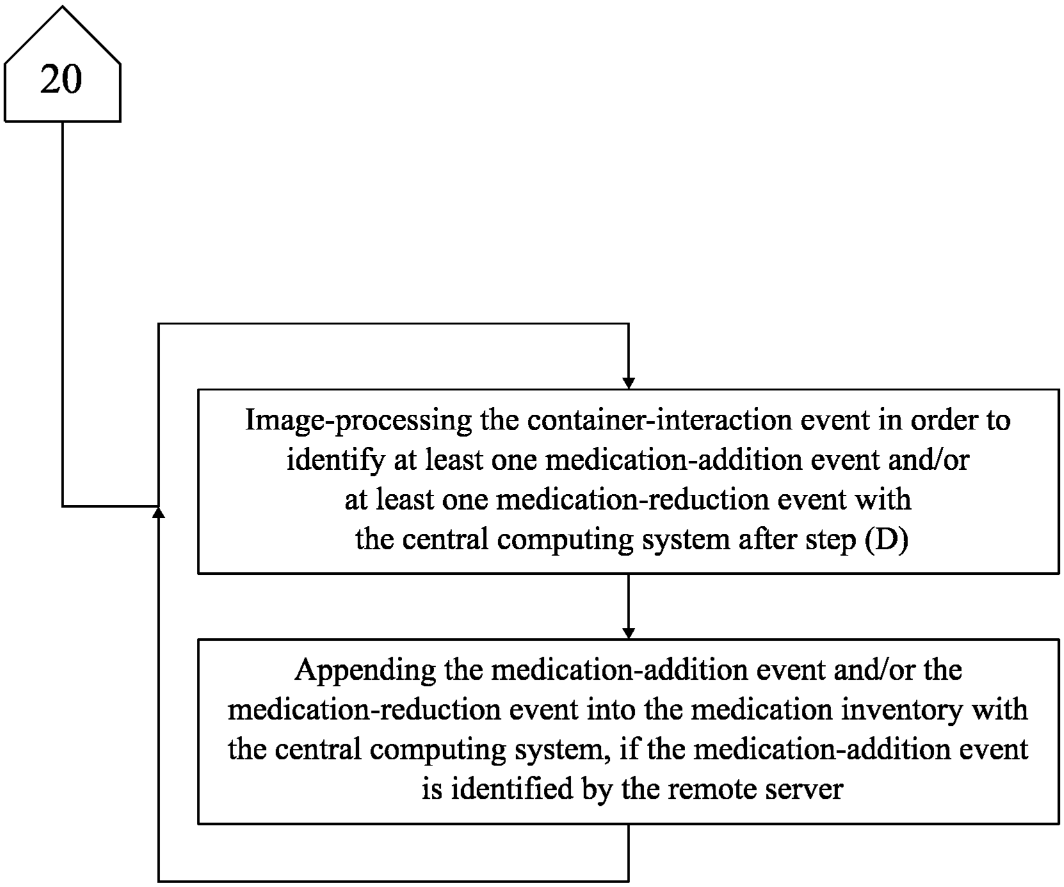
FIG. 21 is a flowchart depicting the subprocess of automatically monitoring the medication inventory of a computerized medication container.

Furthermore, the present invention can include means to automatically keep track of the medication inventory. In one embodiment, the recording of the container-interaction event can also be used to monitor the inventory of the computerized medication container 1. As can be seen in FIG. 21, the subprocess of automatically monitoring the medication inventory of a computerized medication container 1 involves image-processing the container-interaction event in order to identify at least one medication-addition event and/or at least one medication-reduction event with the central computing system after Step D. The at least one medication-addition event occurs when a user replenishes any medication, while the medication-reduction event occurs when a user has taken some medication. Then, the medication-addition event and/or the medication-reduction event is appended into the medication inventory with the central computing system, if the medication-addition event is identified by the central computing system. This way, the medication inventory is kept up to date for when the authorized users want to audit the medication inventory. This subprocess is repeated for a number of iterations to maintain the medication inventory always updated. In other embodiments, different systems and methods can be utilized to maintain the medication inventory updated, such as tracking the weight of a medication container using a weight measurement mechanism, etc.

Figure 22:
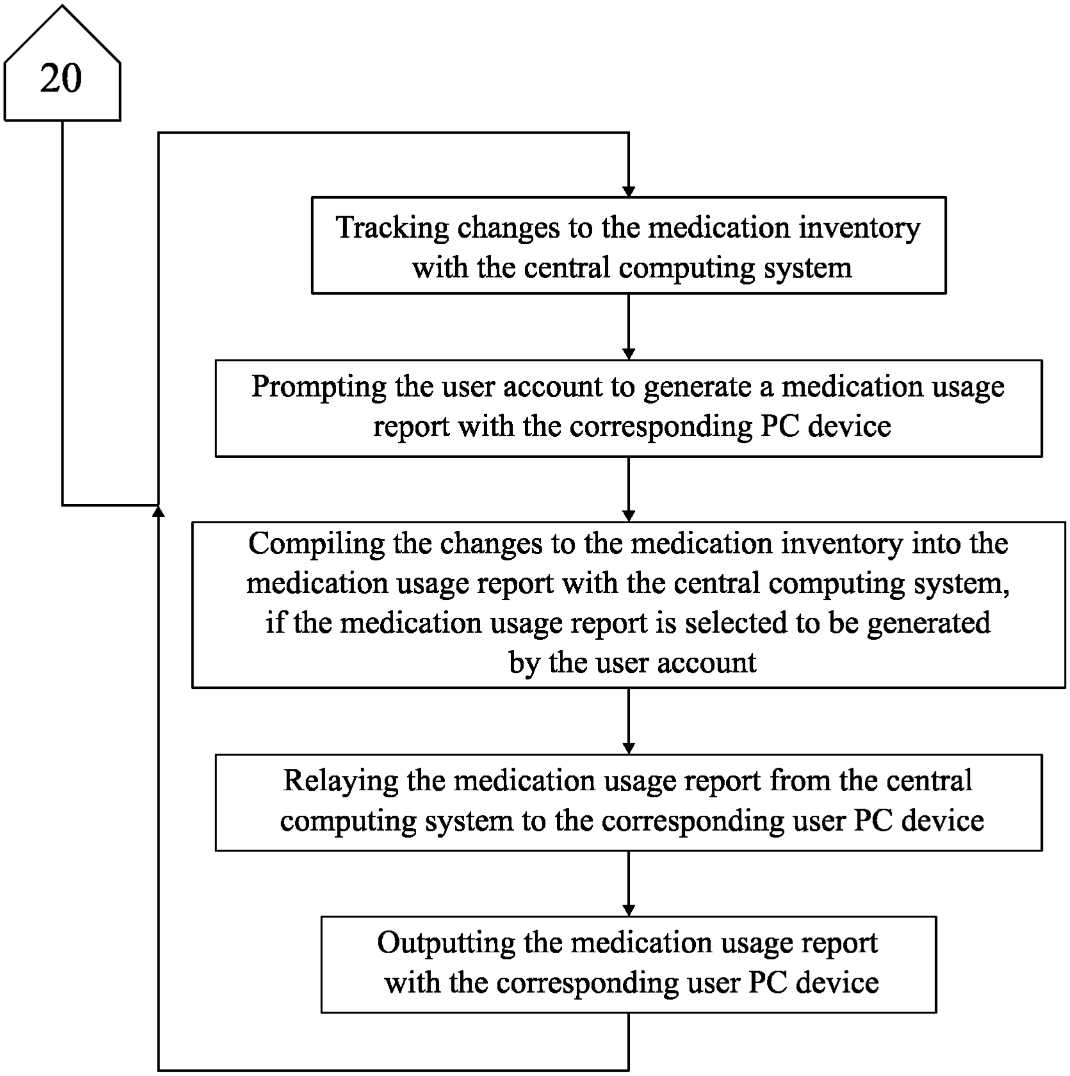
FIG. 22 is a flowchart depicting the subprocess of generating a medication usage report.

Furthermore, the present invention enables the authorized users to control the consumption of medication by a user. For example, parents can track the usage of medication in the household. To do so, the system of the present invention can generate various reports that help authorized users to view the history of medication consumption of various users. As can be seen in FIG. 22, the subprocess of generating a medication usage report involves tracking changes to the medication inventory with the central computing system. For example, the consumption of medication can result in a reduction in the medication that is recorded in the medication inventory. The user account is prompted to generate a medication usage report with the corresponding PC device. The authorized user can do so from the corresponding software application or from the user interface 6 in the computerized medication container 1. Then, the changes to the medication inventory are compiled into the medication usage report with the central computing system, if the medication usage report is selected to be generated by the user account. The medication usage report can be generated in specific formats that are useful to the authorized user. The medication usage report is relayed from the central computing system to the corresponding user PC device, which can then be outputted with the corresponding user PC device. Alternatively, the medication usage report can be exported to other software applications of PC devices. Further, additional reports can be generated that enables authorized users to audit different data compiled in the container event log.

Figure 23:
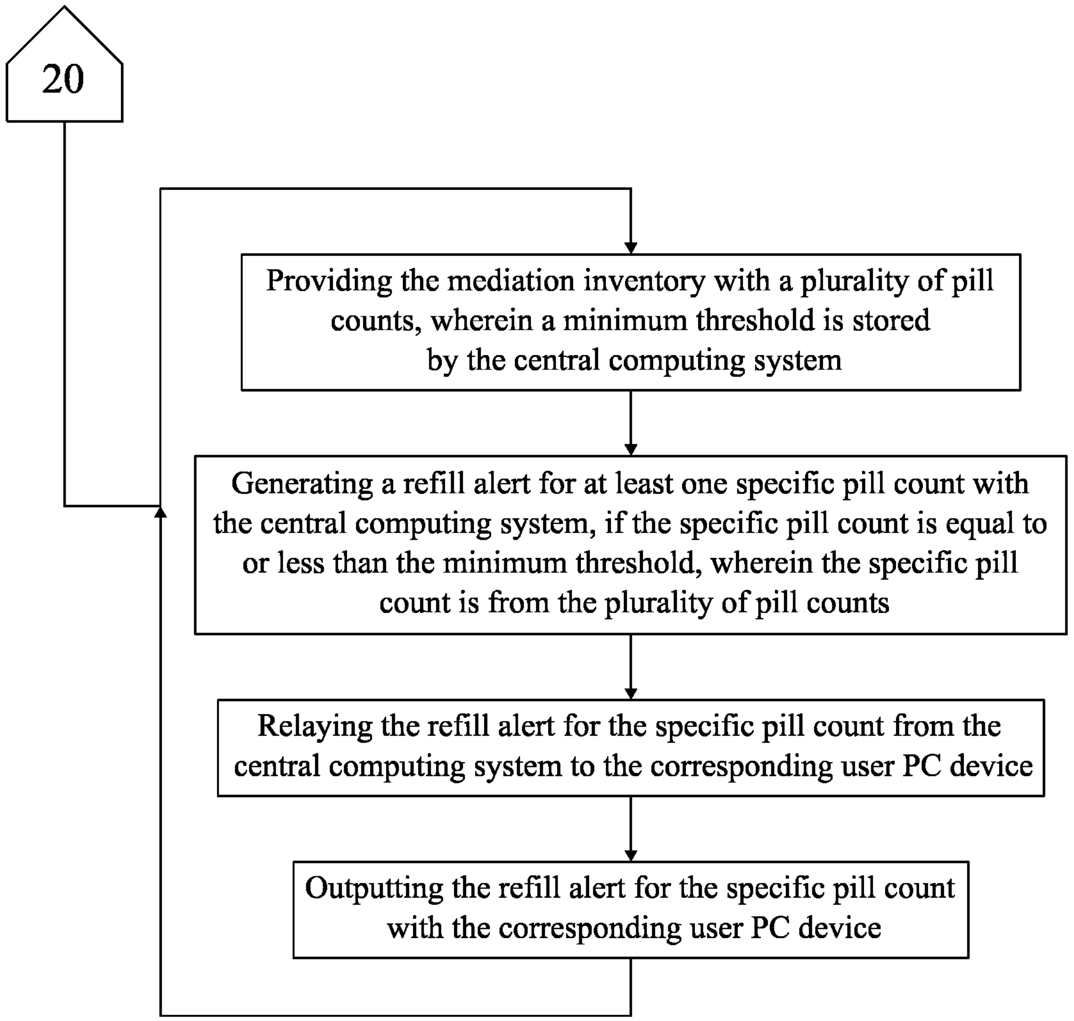
FIG. 23 is a flowchart depicting the subprocess of generating a refill alert for a specific pill count of a medication.

Further, the present invention enables the user to set up alerts or reminders to maintain a desired amount of medicine always available in the computerized medication container 1. This can be automatically using the medication inventory maintained by the system. Medication container refill notifications can be based on periodic medication allotment and frequency counter. As can be seen in FIG. 23, the subprocess of generating a refill alert for the specific pill count of a medication involves providing the mediation inventory with a plurality of pill counts, wherein a minimum threshold is stored by the central computing system. The authorized user can manually input the pill counts and minimum thresholds or enable the access to third-party databases that contain the necessary information. Then, a refill alert is generated for at least one specific pill count with the central computing system, if the specific pill count is equal to or less than the minimum threshold, wherein the specific pill count is from the plurality of pill counts. In other words, the specific pill count reaches the minimum threshold or goes below the minimum threshold, the authorized user is alerted so that the authorized user can take the appropriate actions. Further, the refill alert for the specific pill count is relayed from the central computing system to the corresponding user PC device so that the refill alert for the specific pill count is outputted with the corresponding user PC device. Alternatively, the refill alert can be directly outputted with the user interface 6 or transmitted to a third-party service that is available to the authorized user. Further, other maintenance notifications can be generated such as system health check status events where users can perform system configuration and diagnostics with the help of other users. The present invention can support two-way remote collaboration via the communication module 8 so that the user can perform the right maintenance procedures.

Figure 24:
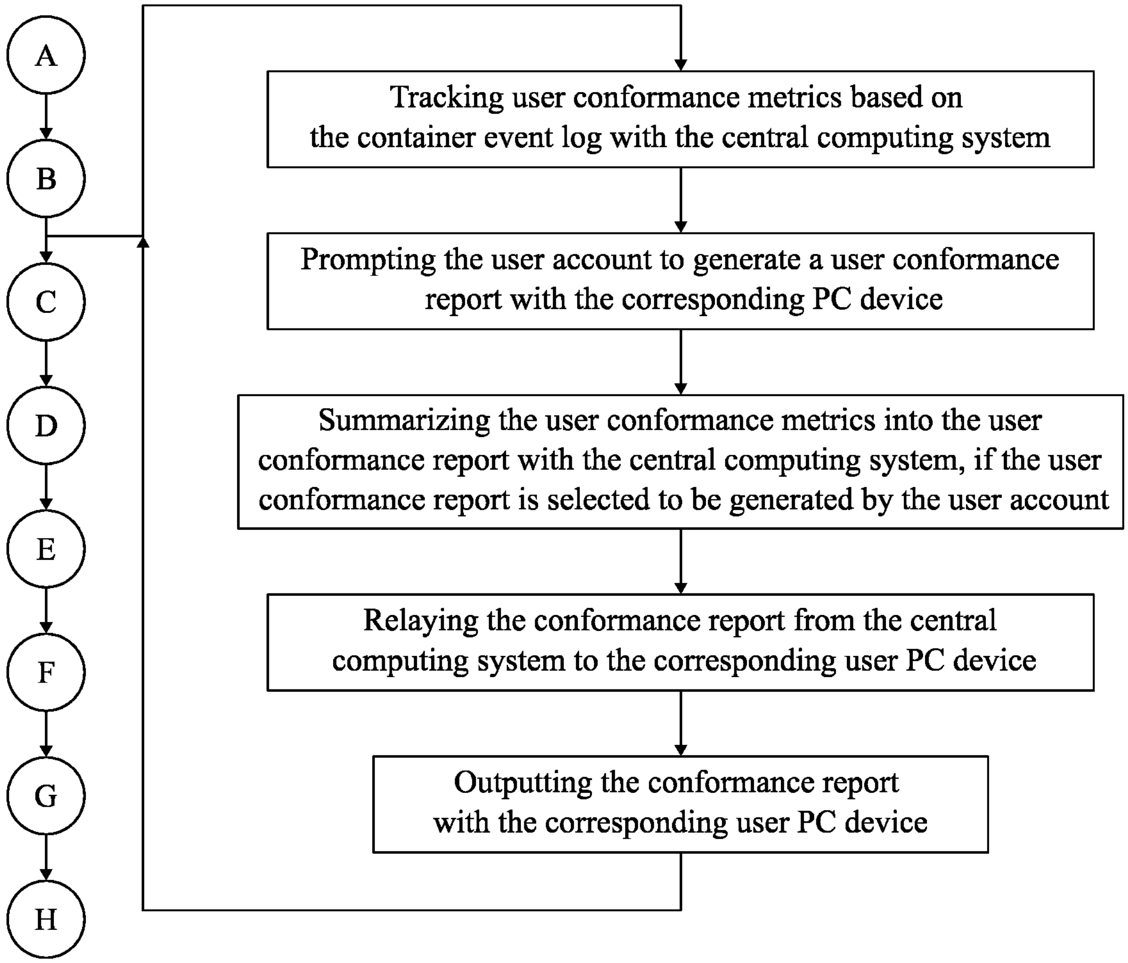
FIG. 24 is a flowchart depicting the subprocess of generating a conformance report of a user.

Furthermore, the authorized users can keep track of the interactions of users with the computerized medication container 1 for different purposes. For example, the authorized users can keep track of how often the users take the medication, how often the users fail to take the medication on time, etc. This can be done by the automatic tracking of various metrics by the present invention which can be presented to the authorized user in the form of a conformance report. As can be seen in FIG. 24, the subprocess of generating the conformance report involves tracking user conformance metrics based on the container event log with the central computing system. The conformance metrics can include, but are not limited to, the punctuality of the user to take the medication, the accuracy of taking the right medication amount, etc. Further, the user account is prompted to generate a user conformance report with the corresponding PC device. Then, the user conformance metrics are summarized into the user conformance report with the central computing system, if the user conformance report is selected to be generated by the user account. The conformance report can be generated in various formats that can be utilized by the authorized user. Then, the user conformance report is relayed from the central computing system to the corresponding user PC device to be outputted with the corresponding user PC device. Alternatively, the conformance report can be directly displayed on the user interface 6 or exported to a third-party service of PC device that is accessible to the authorized user. Furthermore, additional reports can be generated utilizing the user conformance metrics including, but not limited to, usage history of successful medication access prior to non-compliance events.

Although the invention has been explained in relation to its preferred embodiment, it is to be understood that many other possible modifications and variations can be made without departing from the spirit and scope of the invention.

What is claimed is:

1. A method of managing, reminding, and dispensing medication from a controlled-access container, the method comprising the steps of:

(A) providing at least one computerized medication container, wherein the computerized medication container is a customizable container structure configured to store various medications, and wherein the computerized medication container includes at least one processor, at least two restricted access compartments, at least one monitoring camera, at least one mechanical switch, at least one locking mechanism, and an illumination mechanism, and wherein the at least two restricted access compartments, the monitoring camera, the mechanical switch, the locking mechanism, and the illumination mechanism are electronically connected to the processor, and wherein the locking mechanism is operable between a locked configuration that prevents movement of the computerized medication container to a physically-opened configuration and an unlocked configuration that allows movement of the computerized medication container to the physically-opened configuration, and wherein the locking mechanism is an electronic lock operable via at least one central computing system and one or more key fobs, each key fob being associated with an individual user, and wherein the illumination mechanism is configured to ambiently illuminate surroundings of the computerized medication container;

(B) providing at least one user account and at least one container event log managed by the at least one central computing system, wherein the user account is associated with the computerized medication container and a corresponding user personal computing (PC) device, and wherein the container event log is associated with the computerized medication container;

(C) providing at least two access rules managed by the at least one central computing system, wherein a first access rule comprises unlocking, via the locking mechanism, a first restricted access compartment to dispense a first medication to an authorized user and denying the authorized user access to a second restricted access compartment by locking the second restricted access compartment at a first time, and wherein a second access rule comprises checking if the user has taken the first medication, wherein confirmation results in unlocking, via the locking mechanism, a second restricted access compartment to dispense a second medication at a second time;

(D) activating the illumination mechanism and recording a container-interaction event with the monitoring camera, if the mechanical switch is actuated by moving the computerized medication container to the physically-opened configuration;

(E) relaying the container-interaction event from the monitoring camera, through the processor, and to the at least one central computing system, if the container-interaction event is recorded by the monitoring camera;

(F) chronologically appending the container-interaction event into the container event log with the at least one central computing system;

(G) generating a container-interaction alert based on the container-interaction event with the at least one central computing system;

(H) relaying the container-interaction alert from the at least one central computing system to the corresponding user PC device;

(I) outputting the container-interaction alert with the corresponding user PC device; and (J) sequentially executing steps (C) through (I).

2. The method as claimed in claim 1 comprising the steps of: prompting the user account to view the container-interaction event with the corresponding user PC device after step (I); relaying the container-interaction event from the central computing system to the corresponding user PC device, if the container-interaction event is selected to be viewed by the user account; and outputting the container-interaction event with the corresponding user PC device.

3. The method as claimed in claim 1 comprising the steps of: providing a plurality of medication reminders for the user account managed by the central computing system; tracking a current date-and-time with the central computing system; comparing the current date-and-time to each medication reminder with the central computing system in order to identify at least one matching reminder from the plurality of medication reminders, wherein the matching reminder is within a reminder window of the current date-and-time; comparing the current date-and-time to the client event log with the central computing system in order to identify a matching log from the client event log, wherein the matching log is within the reminder window of the current date-and-time; generating a missed-medication alert with the central computing system, if the matching reminder is identified from the plurality of medication reminders, and if the matching log is not identified from the client event log; relaying the missed-medication alert from the central computing system to the corresponding user PC device; and outputting the missed-medication alert with the corresponding user PC device.

4. The method as claimed in claim 1 comprising the steps of: logging a lock-released event with the processor, if the mechanical switch is actuated by moving the computerized medication container to the physically-opened configuration, and if the locking mechanism is set to an unlocked configuration; relaying the lock-released event from the processor to the central computing system, if the lock-released event is logged by the processor; chronologically appending the lock-release event into the container event log with the central computing system; generating a lock-released alert based on the lock-release event with the central computing system; relaying the lock-released alert from the central computing system to the corresponding user PC device; and outputting the lock-released alert with the corresponding user PC device.

5. The method as claimed in claim 1 comprising the steps of: logging a lock-broken event with the processor, if the mechanical switch is actuated by moving the computerized medication container to the physically-opened configuration, and if the locking mechanism is set to the locked configuration; relaying the lock-broken event from the processor to the central computing system, if the lock-broken event is logged by the processor; chronologically appending the lock-broken event into the container event log with the central computing system; generating a lock-broken alert based on the lock-broken event with the central computing system; relaying the lock-broken alert from the central computing system to the corresponding user PC device; and outputting the lock-broken alert with the corresponding user PC device.

6. The method as claimed in claim 1 comprising the steps of: providing the computerized medication container with a motion sensor, wherein the motion sensor is electronically connected to the processor; logging a close-proximity event with the processor, if a physical object is detected near the computerized medication container by the motion sensor; relaying the close-proximity event from the processor to the central computing system, if the close-proximity event is logged by the processor; chronologically appending the close-proximity event into the container event log with the central computing system; generating a close-proximity alert based on the close-proximity event with the central computing system; relaying the close-proximity alert from the central computing system to the corresponding user PC device; and outputting the close-proximity alert with the corresponding user PC device.

7. The method as claimed in claim 1 comprising the steps of: providing the computerized medication container with a visual recording indicator, wherein the visual recording indicator is electronically connected to the processor; activating the visual recording indicator during step (D); and deactivating the visual recording indicator after step (D).

8. The method as claimed in claim 1 comprising the steps of: providing the computerized medication container with an output device, wherein the output device is electronically connected to the processor; prompting the user account to enter at least one user alert with the corresponding user PC device; relaying the user alert from the corresponding user PC device, through the central computing system, and to the processor, if the user alert is entered by the user account; and outputting the user alert with the output device, if the mechanical switch is actuated by moving the computerized medication container to the physically-opened configuration.

9. The method as claimed in claim 1 comprising the steps of: providing the computerized medication container with an output device, wherein the output device is electronically connected to the processor; prompting the user account to enter at least one user instruction with the corresponding user PC device; relaying the user instruction from the corresponding user PC device, through the central computing system, and to the processor, if the user instruction is entered by the user account; and outputting the user instruction with the output device, if the mechanical switch is actuated by moving the computerized medication container to the physically-opened configuration.

10. The method as claimed in claim 1 comprising the steps of: providing the computerized medication container with a communication mechanism, wherein the communication mechanism is electronically connected to the processor; generating an activation alert with the processor, if the mechanical switch is actuated by moving the computerized medication container to the physically-opened configuration; relaying the activation alert from the processor, through the central computing system, and to the corresponding user PC device, if the activation alert is generated by the processor; and outputting the activation alert with the corresponding user PC device.

11. The method as claimed in claim 10 comprising the steps of: receiving at least one user instruction through the corresponding user PC device; relaying the user instruction from the corresponding user PC device, through the central computing system, and to the processor; and outputting the user instruction with the communication mechanism.

12. The method as claimed in claim 10 comprising the steps of: receiving at least one response through the communication mechanism; relaying the response from the processor, through the central computing system, and to the corresponding user PC device; and outputting the response with the corresponding user PC device.

13. The method as claimed in claim 1 comprising the steps of: tracking at least one access condition for the first restricted access compartment with the processor; logging an unauthorized-access event with the processor, if the access rule is not satisfied by the access condition, and if the restricted access compartment is in a physically-opened configuration; relaying the unauthorized-access event from the processor to the central computing system, if the unauthorized-access event is logged by the processor; chronologically appending the unauthorized-access event into the container event log with the central computing system; generating an unauthorized-access alert based on the unauthorized-access event with the central computing system; relaying the unauthorized-access alert from the central computing system to the corresponding user PC device; and outputting the unauthorized-access alert with the corresponding user PC device.

14. The method as claimed in claim 13 comprising the steps of: prompting the user account to enter at least one new access rule with the corresponding user PC device; relaying the new access rule from the corresponding user PC device, through the central computing system, and to the processor, if the new access rule is entered by the user account; and applying the new access rule to the restricted access compartment with the processor.

15. The method as claimed in claim 1 comprising the steps of: providing a medication inventory managed by the central computing system, wherein the medication inventory is associated with the computerized medication container; prompting the user account to view the medication inventory with the corresponding user PC device; relaying the medication inventory from the central computing system to the corresponding user PC device, if the medication inventory is selected to be viewed by the user account; and outputting the medication inventory with the corresponding user PC device.

16. The method as claimed in claim 15 comprising the steps of: image processing the container-interaction event in order to identify at least one medication-addition event and/or at least one medication-reduction event with the central computing system after step (E); and appending the medication-addition event and/or the medication-reduction event into the medication inventory with the central computing system, if the medication-addition event is identified by the central computing system.

17. The method as claimed in claim 15 comprising the steps of: tracking changes to the medication inventory with the central computing system; prompting the user account to generate a medication usage report with the corresponding PC device; compiling the changes to the medication inventory into the medication usage report with the central computing system, if the medication usage report is selected to be generated by the user account; relaying the medication usage report from the central computing system to the corresponding user PC device; and outputting the medication usage report with the corresponding user PC device.

18. The method as claimed in claim 15 comprising the steps of: providing the medication inventory with a plurality of pill counts, wherein a minimum threshold is stored by the central computing system; generating a refill alert for at least one specific pill count with the central computing system, if the specific pill count is equal to or less than the minimum threshold, wherein the specific pill count is from the plurality of pill counts; relaying the refill alert for the specific pill count from the central computing system to the corresponding user PC device; and outputting the refill alert for the specific pill count with the corresponding user PC device.

19. The method as claimed in claim 1 comprising the steps of: tracking user conformance metrics based on the container event log with the central computing system; prompting the user account to generate a user conformance report with the corresponding PC device; summarizing the user conformance metrics into the user conformance report with the central computing system, if the user conformance report is selected to be generated by the user account; relaying the user conformance report from the central computing system to the corresponding user PC device; and outputting the user conformance report with the corresponding user PC device.

20. The method as claimed in claim 1 comprising the steps of: detecting with the processor when the locking mechanism moves from the locked configuration to the unlocked configuration or vice versa.

21. The method as claimed in claim 20 comprising the steps of: detecting with the processor which key fob has been used to move the locking mechanism from the locked configuration to the unlocked configuration or vice versa.

* * * * *